United States Patent
Moffitt et al.

(10) Patent No.: US 10,449,360 B2
(45) Date of Patent: *Oct. 22, 2019

(54) GRAPHICAL USER INTERFACE FOR PROGRAMMING NEUROSTIMULATION PULSE PATTERNS

(71) Applicant: Boston Scientific Neuromodulation Corporation, Valencia, CA (US)

(72) Inventors: Michael A. Moffitt, Saugus, CA (US); Sridhar Kothandaraman, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 99 days.

This patent is subject to a terminal disclaimer.

(21) Appl. No.: 15/670,328

(22) Filed: Aug. 7, 2017

(65) Prior Publication Data

US 2017/0333718 A1 Nov. 23, 2017

Related U.S. Application Data

(63) Continuation of application No. 14/853,589, filed on Sep. 14, 2015, now Pat. No. 9,737,717.

(Continued)

(51) Int. Cl.
*A61N 1/36* (2006.01)
*A61N 1/08* (2006.01)
(Continued)

(52) U.S. Cl.
CPC .......... *A61N 1/36146* (2013.01); *A61N 1/05* (2013.01); *A61N 1/08* (2013.01); *A61N 1/36125* (2013.01);
(Continued)

(58) Field of Classification Search
CPC ... A61N 1/05; A61N 1/08; A61N 1/36; A61N 1/36125; A61N 1/36128; A61N 1/36132; A61N 1/36146; A61N 1/37247
(Continued)

(56) References Cited

U.S. PATENT DOCUMENTS 4,255,790 A 3/1981 Hondeghem
4,931,858 A 6/1990 Honjo et al.
(Continued)

FOREIGN PATENT DOCUMENTS

AU 2015318142 B2 6/2018
AU 2015343483 B2 6/2018
(Continued)

OTHER PUBLICATIONS

U.S. Appl. No. 14/853,589, U.S. Pat. No. 9,737,717, filed Sep. 14, 2015, Graphical User Interface for Programming Neurostimulation Pulse Patterns.
(Continued)

*Primary Examiner* — Christopher A Flory
(74) *Attorney, Agent, or Firm* — Schwegman Lundberg & Woessner, P.A.

(57) ABSTRACT

An example of a neurostimulation system may include a storage device, a programming control circuit, and a graphical user interface (GUI). The storage device may be configured to store individually definable waveforms. The programming control circuit may be configured to generate stimulation parameters controlling the delivery of the neurostimulation pulses according to a pattern. The GUI may be configured to define the pattern using one or more waveforms selected from the individually definable waveforms. The GUI may display waveform tags each selectable for access to a waveform of the individually definable waveforms, and display a waveform builder in response to
(Continued)

selection of one of the waveform tags. The waveform builder may present a graphical representation of the accessed waveform and allow for the accessed waveform to be adjusted by editing the graphical representation of the accessed waveform on the GUI.

20 Claims, 16 Drawing Sheets

Related U.S. Application Data

(60) Provisional application No. 62/050,505, filed on Sep. 15, 2014.

(51) Int. Cl.
*A61N 1/05* (2006.01)
*A61N 1/372* (2006.01)

(52) U.S. Cl.
CPC ..... *A61N 1/37247* (2013.01); *A61N 1/37264* (2013.01)

(58) Field of Classification Search
USPC ...................................................... 607/59, 72
See application file for complete search history.

(56) References Cited

U.S. PATENT DOCUMENTS

| | | | |
|---|---|---|---|
| 4,935,674 A | 6/1990 | Rodriguez-cavazos | |
| 5,300,096 A | 4/1994 | Hall et al. | |
| 5,360,437 A | 11/1994 | Thompson | |
| 5,369,224 A | 11/1994 | Miyata | |
| 5,381,524 A * | 1/1995 | Lewis | G06F 17/5031 715/255 |
| 5,576,979 A * | 11/1996 | Lewis | G06F 17/5031 715/700 |
| 5,713,937 A | 2/1998 | Nappholz et al. | |
| 5,724,985 A | 3/1998 | Snell et al. | |
| 5,725,560 A | 3/1998 | Brink | |
| 6,266,566 B1 | 7/2001 | Nichols et al. | |
| 6,516,227 B1 | 2/2003 | Meadows et al. | |
| 6,675,046 B2 | 1/2004 | Holsheimer | |
| 6,895,280 B2 | 5/2005 | Meadows et al. | |
| 6,993,384 B2 | 1/2006 | Bradley et al. | |
| 7,003,349 B1 | 2/2006 | Andersson et al. | |
| 7,228,179 B2 | 6/2007 | Campen et al. | |
| 7,317,948 B1 | 1/2008 | King et al. | |
| 7,333,856 B1 | 2/2008 | Er et al. | |
| 7,333,857 B2 | 2/2008 | Campbell | |
| 7,539,538 B2 | 5/2009 | Parramon et al. | |
| 7,650,184 B2 | 1/2010 | Walter | |
| 7,664,849 B1 | 2/2010 | Chandler et al. | |
| 7,783,353 B2 | 8/2010 | Libbus et al. | |
| 7,826,901 B2 | 11/2010 | Lee et al. | |
| 7,979,119 B2 | 7/2011 | Kothandaraman et al. | |
| 7,979,133 B2 | 7/2011 | Feler et al. | |
| 7,983,762 B2 | 7/2011 | Gliner et al. | |
| 8,019,439 B2 | 9/2011 | Kuzma et al. | |
| 8,224,453 B2 | 7/2012 | De Ridder | |
| 8,255,057 B2 | 8/2012 | Fang et al. | |
| 8,285,389 B2 | 10/2012 | Libbus et al. | |
| 8,340,775 B1 | 12/2012 | Cullen et al. | |
| 8,355,797 B2 | 1/2013 | Caparso et al. | |
| 8,455,716 B2 | 6/2013 | Huang et al. | |
| 8,504,147 B2 | 8/2013 | Deem et al. | |
| 8,560,080 B2 | 10/2013 | Goetz | |
| 8,615,300 B2 | 12/2013 | Feler et al. | |
| 8,649,874 B2 | 2/2014 | Alataris et al. | |
| 8,670,831 B2 | 3/2014 | Wacnik et al. | |
| 8,676,329 B2 | 3/2014 | Wacnik et al. | |
| 8,676,331 B2 | 3/2014 | Parker | |
| 8,692,843 B2 | 4/2014 | Bloemer | |
| 8,694,113 B2 | 4/2014 | Smoorenburg | |
| 8,731,675 B2 | 5/2014 | Ranu et al. | |
| 8,751,009 B2 | 6/2014 | Wacnik | |
| 8,798,755 B2 | 8/2014 | Grill et al. | |
| 8,874,211 B2 | 10/2014 | Libbus et al. | |
| 9,265,948 B2 | 2/2016 | Libbus et al. | |
| 9,737,717 B2 | 8/2017 | Moffitt et al. | |
| 9,802,052 B2 | 10/2017 | Marnfeldt | |
| 2002/0077669 A1 | 6/2002 | Lindh et al. | |
| 2002/0077859 A1 | 6/2002 | Stahmann et al. | |
| 2002/0115939 A1 | 8/2002 | Mulligan et al. | |
| 2003/0139781 A1 | 7/2003 | Bradley et al. | |
| 2003/0176899 A1 | 9/2003 | Samuelsson et al. | |
| 2004/0111131 A1 | 6/2004 | Hu et al. | |
| 2005/0177206 A1 | 8/2005 | North et al. | |
| 2006/0149337 A1 | 7/2006 | John | |
| 2006/0241720 A1 | 10/2006 | Woods et al. | |
| 2007/0150036 A1 | 6/2007 | Anderson | |
| 2007/0299663 A1 | 12/2007 | Fado et al. | |
| 2008/0158175 A1 | 7/2008 | Hotelling et al. | |
| 2008/0163097 A1 | 7/2008 | Goetz et al. | |
| 2008/0188909 A1 | 8/2008 | Bradley | |
| 2009/0024189 A1 | 1/2009 | Lee et al. | |
| 2009/0043359 A1 | 2/2009 | Smoorenburg | |
| 2009/0198305 A1 | 8/2009 | Naroditsky et al. | |
| 2009/0204173 A1 | 8/2009 | Fang et al. | |
| 2010/0010390 A1 | 1/2010 | Skelton et al. | |
| 2010/0010566 A1 | 1/2010 | Thacker et al. | |
| 2010/0010646 A1 | 1/2010 | Drew et al. | |
| 2010/0121409 A1 | 5/2010 | Kothandaraman et al. | |
| 2010/0274312 A1 | 10/2010 | Alataris et al. | |
| 2010/0274314 A1 | 10/2010 | Alataris et al. | |
| 2010/0274315 A1 | 10/2010 | Alataris et al. | |
| 2010/0274317 A1 | 10/2010 | Parker et al. | |
| 2010/0274318 A1 | 10/2010 | Walker et al. | |
| 2010/0274326 A1 | 10/2010 | Chitre et al. | |
| 2011/0046697 A1 | 2/2011 | Gerber et al. | |
| 2011/0054570 A1 | 3/2011 | Lane | |
| 2011/0093051 A1 | 4/2011 | Davis et al. | |
| 2011/0208012 A1 | 8/2011 | Gerber et al. | |
| 2012/0059446 A1 | 3/2012 | Wallace et al. | |
| 2012/0083709 A1 | 4/2012 | Parker et al. | |
| 2012/0109006 A1 | 5/2012 | James et al. | |
| 2012/0197336 A1 | 8/2012 | Su | |
| 2012/0253422 A1 | 10/2012 | Thacker et al. | |
| 2012/0265267 A1 | 10/2012 | Blum et al. | |
| 2012/0265279 A1 | 10/2012 | Zhu et al. | |
| 2012/0283797 A1 | 11/2012 | De Ridder | |
| 2012/0290041 A1 | 11/2012 | Kim et al. | |
| 2012/0296396 A1 | 11/2012 | Moffitt et al. | |
| 2012/0302912 A1 | 11/2012 | Moffitt et al. | |
| 2013/0041283 A1 | 2/2013 | Wichner | |
| 2013/0053926 A1 | 2/2013 | Hincapie Ordonez et al. | |
| 2013/0060304 A1 | 2/2013 | Wichner | |
| 2013/0066411 A1 | 3/2013 | Thacker et al. | |
| 2013/0116752 A1 | 5/2013 | Parker et al. | |
| 2013/0131760 A1 | 5/2013 | Rao et al. | |
| 2013/0226261 A1 | 8/2013 | Sparks et al. | |
| 2013/0268021 A1 | 10/2013 | Moffitt | |
| 2013/0268026 A1 | 10/2013 | Rao et al. | |
| 2013/0296975 A1 | 11/2013 | Lee et al. | |
| 2013/0304152 A1 | 11/2013 | Bradley et al. | |
| 2014/0005743 A1 | 1/2014 | Giuffrida et al. | |
| 2014/0052033 A1 | 2/2014 | Lawlis et al. | |
| 2014/0067016 A1 | 3/2014 | Kaula et al. | |
| 2014/0074179 A1 | 3/2014 | Heldman et al. | |
| 2014/0074180 A1 | 3/2014 | Heldman et al. | |
| 2014/0074190 A1 | 3/2014 | Griffith | |
| 2014/0081349 A1 | 3/2014 | Lee et al. | |
| 2014/0081354 A1 | 3/2014 | Davis et al. | |
| 2014/0172045 A1 | 6/2014 | Yip et al. | |
| 2014/0257425 A1 | 9/2014 | Arcot-krishnamurthy et al. | |
| 2014/0257428 A1 | 9/2014 | Zhu | |
| 2014/0276181 A1 | 9/2014 | Sun et al. | |
| 2014/0277267 A1 | 9/2014 | Vansickle et al. | |
| 2015/0012057 A1 | 1/2015 | Carlson et al. | |
| 2015/0051666 A1 | 2/2015 | Roy et al. | |
| 2015/0165209 A1 | 6/2015 | Grandhe et al. | |
| 2015/0224307 A1 | 8/2015 | Bolea | |
| 2015/0238762 A1 | 8/2015 | Pal et al. | |

(56) References Cited

U.S. PATENT DOCUMENTS

| | | | |
|---|---|---|---|
| 2015/0297893 A1 | 10/2015 | Kokones et al. |
| 2015/0328461 A1 | 11/2015 | Charlesworth et al. |
| 2015/0328462 A1 | 11/2015 | Griffith |
| 2015/0328467 A1 | 11/2015 | Demers et al. |
| 2015/0343242 A1 | 12/2015 | Tyler et al. |
| 2016/0027293 A1 | 1/2016 | Esteller et al. |
| 2016/0074662 A1 | 3/2016 | Moffitt et al. |
| 2016/0074663 A1 | 3/2016 | De Ridder |
| 2016/0121126 A1 | 5/2016 | Marnfeldt |
| 2016/0279429 A1 | 9/2016 | Hershey et al. |
| 2017/0050033 A1 | 2/2017 | Wechter |
| 2017/0106197 A1 | 4/2017 | Wechter et al. |

FOREIGN PATENT DOCUMENTS

| | | | |
|---|---|---|---|
| CN | 106687173 A | 5/2017 |
| CN | 107073269 A | 8/2017 |
| CN | 107921255 A | 4/2018 |
| CN | 108463266 A | 8/2018 |
| EP | 3194021 B1 | 10/2018 |
| JP | 1057508 A | 3/1998 |
| JP | 2010534114 A | 11/2010 |
| JP | 2013533092 A | 8/2013 |
| JP | 2014518722 A | 8/2014 |
| JP | 2017527429 A | 9/2017 |
| JP | 2017533072 A | 11/2017 |
| WO | WO-03051175 A2 | 6/2003 |
| WO | WO-3051175 A2 | 6/2003 |
| WO | WO-2006029257 A2 | 3/2006 |
| WO | WO-2006135791 A2 | 12/2006 |
| WO | WO-2009067610 A1 | 5/2009 |
| WO | WO-2014159880 A1 | 10/2014 |
| WO | WO-2016004230 A1 | 1/2016 |
| WO | WO-2016044169 A1 | 3/2016 |
| WO | WO-2016073271 A1 | 5/2016 |
| WO | WO-2016154375 A1 | 9/2016 |
| WO | WO-2016172239 A1 | 10/2016 |
| WO | WO-2017019191 A1 | 2/2017 |
| WO | WO-2017066187 A1 | 4/2017 |

OTHER PUBLICATIONS

U.S. Appl. No. 14/926,725, filed Oct. 29, 2015, Method and Apparatus for Programming Complex Neurostimulation Patterns.
U.S. Appl. No. 15/079,340, filed Mar. 24, 216, Method and Apparatus for Controlling Temporal Patterns of Neurostimulation.
U.S. Appl. No. 15/180,980, filed Jun. 13, 2016, User Interface for Custom Patterned Electrical Stimulation.
U.S. Appl. No. 15/290,776, filed Oct. 11, 2016, User Interface for Neurostimulation Waveform Composition.
"U.S. Appl. No. 14/853,589, Final Office Action dated Jan. 18, 2017", 12 pgs.
"U.S. Appl. No. 14/853,589, Non Final Office Action dated Aug. 17, 2016", 14 pgs.
"U.S. Appl. No. 14/853,589, Notice of Allowance dated Apr. 17, 2017", 5 pgs.
"U.S. Appl. No. 14/853,589, Response filed Mar. 14, 2017 to Final Office Action dated Jan. 18, 2017", 12 pgs.
"U.S. Appl. No. 14/853,589, Response filed Nov. 17, 2016 to Non Final Office Action dated Aug. 17, 2016", 12 pgs.
"International Application Serial No. PCT/US15/58017, International Search Report dated Apr. 6, 2016", 5 pgs.
"International Application Serial No. PCT/US15/58017, Written Opinion dated Apr. 6, 2016", 8 pgs.
"International Application Serial No. PCT/US2015/049993, International Search Report dated Jan. 14, 2016", 3 pgs.
"International Application Serial No. PCT/US2015/049993, Written Opinion dated Jan. 14, 2016", 4 pgs.
"International Application Serial No. PCT/US2016/023888, International Search Report dated Jun. 6, 2016", 5 pgs.
"International Application Serial No. PCT/US2016/023888, Written Opinion dated Jun. 6, 2016", 5 pgs.
"International Application Serial No. PCT/US2016/037226, International Search Report dated Aug. 25, 2016", 4 pgs.
"International Application Serial No. PCT/US2016/037226, Written Opinion dated Aug. 25, 2016", 5 pgs.
Rao, Prakash, et al., "Technique for Linking Electrodes Together During Programming of Neurostimulation System", U.S. Appl. No. 61/561,760, filed Nov. 18, 2011.
Vansickle, Dennis Allen, et al., "Neuromodulation System and Method for Transitioning Between Programming Modes", U.S. Appl. No. 14/214,752, filed Mar. 15, 2014.
Vansickle, Dennis Allen, "Systems and Methods for Delivering Sub-Threshold Therapy to a Patient", U.S. Appl. No. 61/801,917, filed Mar. 15, 2013.
"U.S. Appl. No. 14/926,725, Corrected Notice of Allowance dated Jul. 17, 2017", 2 pgs.
"U.S. Appl. No. 14/926,725, Non Final Office Action dated Mar. 3, 2017", 13 pgs.
"U.S. Appl. No. 14/926,725, Notice of Allowability dated Jul. 28, 2017", 2 pgs.
"U.S. Appl. No. 14/926,725, Notice of Allowance dated Jun. 27, 2017", 8 pgs.
"U.S. Appl. No. 14/926,725, Response filed May 25, 2017 to Non Final Office Action dated Mar. 3, 2017", 12 pgs.
"U.S. Appl. No. 15/079,340, Advisory Action dated Apr. 8, 2019", 3 pgs.
"U.S. Appl. No. 15/079,340, Advisory Action dated Jun. 21, 2018", 3 pgs.
"U.S. Appl. No. 15/079,340, Examiner Interview Summary dated Mar. 5, 2019", 3 pgs.
"U.S. Appl. No. 15/079,340, Final Office Action dated Jan. 10, 2019", 13 pgs.
"U.S. Appl. No. 15/079,340, Final Office Action dated Apr. 4, 2018", 12 pgs.
"U.S. Appl. No. 15/079,340, Non Final Office Action dated Jul. 27, 2018", 12 pgs.
"U.S. Appl. No. 15/079,340, Non Final Office Action dated Oct. 3, 2017", 10 pgs.
"U.S. Appl. No. 15/079,340, Response filed Mar. 4, 2019 to Final Office Action dated Jan. 10, 2019", 12 pgs.
"U.S. Appl. No. 15/079,340, Response filed Jun. 4, 2018 to Final Office Action dated Apr. 4, 2018", 10 pgs.
"U.S. Appl. No. 15/079,340, Response filed Oct. 29, 2018 to Non Final Office Action dated Jul. 27, 2018", 10 pgs.
"U.S. Appl. No. 15/079,340, Response filed Dec. 20, 2017 to Non Final Office Action dated Oct. 3, 2017", 10 pgs.
"U.S. Appl. No. 15/180,980, Advisory Action dated May 24, 2018", 5 pgs.
"U.S. Appl. No. 15/180,980, Examiner Interview Summary dated Apr. 30, 2018", 3 pgs.
"U.S. Appl. No. 15/180,980, Examiner Interview Summary dated Oct. 10, 2018", 3 pgs.
"U.S. Appl. No. 15/180,980, Final Office Action dated Mar. 1, 2018", 10 pgs.
"U.S. Appl. No. 15/180,980, Non Final Office Action dated Jul. 19, 2018", 10 pgs.
"U.S. Appl. No. 15/180,980, Non Final Office Action dated Sep. 21, 2017", 9 pgs.
"U.S. Appl. No. 15/180,980, Notice of Allowance dated Feb. 14, 2019", 9 pgs.
"U.S. Appl. No. 15/180,980, Repsonse filed Dec. 20, 2017 to Non Final Office Action dated Sep. 21, 2017", 15 pgs.
"U.S. Appl. No. 15/180,980, Response filed Jul. 2, 2018 to Advisory Action dated May 24, 2018", 11 pgs.
"U.S. Appl. No. 15/180,980, Response filed Oct. 8, 2018 to Non Final Office Action dated Jul. 19, 2018", 12 pgs.
"U.S. Appl. No. 15/290,776, Examiner Interview Summary dated Oct. 12, 2018", 3 pgs.
"U.S. Appl. No. 15/290,776, Final Office Action dated Jan. 31, 2019", 24 pgs.
"U.S. Appl. No. 15/290,776, Non Final Office Action dated Jul. 12, 2018", 18 pgs.

(56) References Cited

OTHER PUBLICATIONS

"U.S. Appl. No. 15/290,776, Response filed Oct. 8, 2018 to Non Final Office Action dated Jul. 12, 2018", 11 pgs.

"U.S. Appl. No. 15/290,776, Response filed Mar. 19, 2019 to Final Office Action dated Jan. 31, 2019", 8 pgs.

"Australian Application Serial No. 2015318142, First Examiners Report dated Sep. 15, 2017", 3 pgs.

"Australian Application Serial No. 2015318142, Response filed Feb. 8, 2018 to First Examiners Report dated Sep. 15, 2017", 15 pgs.

"Australian Application Serial No. 2015343483, First Examiners Report dated Sep. 19, 2017", 3 pgs.

"Australian Application Serial No. 2015343483, Response filed Feb. 8, 2018 to First Examiners Report dated Sep. 19, 2017", 17 pgs.

"Australian Application Serial No. 2016297965, First Examination Report dated Jun. 19, 2018", 3 pgs.

"Australian Application Serial No. 2016297965, Response filed Feb. 22, 2019 to First Examination Report dated Jun. 19, 2018", 13 pgs.

"Australian Application Serial No. 2018202528, First Examination Report dated Dec. 21, 2018", 3 pgs.

"Chinese Application Serial No. 201580048568.3, Office Action dated Mar. 28, 2019", w/ English Translation, 26 pgs.

"Chinese Application Serial No. 201580048568.3, Office Action dated Jul. 31, 2018", with English translation, 24 pgs.

"Chinese Application Serial No. 201580048568.3, Response filed Dec. 13, 2018 to Office Action dated Jul. 31, 2018", w/ English claims, 70 pgs.

"European Application Serial No. 15767069.6, Response filed Nov. 23, 2017 to Communication Pursuant to Rules 161 and 162 EPC dated May 19, 2017", 12 pgs.

"European Application Serial No. 15791183.5, Response filed Feb. 6, 2018 to Communication Pursuant to Rules 161 & 162 EPC dated Jul. 27, 2017", 12 pgs.

"European Application Serial No. 16732137.1, Response filed Oct. 15, 2018 to Communication Pursuant to Rules 161 and 162 EPC dated Apr. 3, 2018", 10 pgs.

"European Application Serial No. 16784712.8, Response filed Dec. 14, 2018 to Communication Pursuant to Rules 161 and 162 dated Jun. 4, 2018", 15 pgs.

"European Application Serial No. 18201843.2, Extended European Search Report dated Jan. 2, 2019", 6 pgs.

"International Application Serial No. PCT/US2015/049993, International Preliminary Report on Patentability dated Mar. 30, 2017", 6 pgs.

"International Application Serial No. PCT/US2015/058017, International Preliminary Report on Patentability dated May 18, 2017", 10 pgs.

"International Application Serial No. PCT/US2016/023888, International Preliminary Report on Patentability dated Oct. 5, 2017", 7 pgs.

"International Application Serial No. PCT/US2016/037226, International Preliminary Report on Patentability dated Feb. 8, 2018", 7 pgs.

"International Application Serial No. PCT/US2016/056426, International Preliminary Report on Patentability dated Apr. 26, 2018", 8 pgs.

"International Application Serial No. PCT/US2016/056426, International Search Report dated Jan. 26, 2017", 5 pgs.

"International Application Serial No. PCT/US2016/056426, Written Opinion dated Jan. 26, 2017", 6 pgs.

"Japanese Application Serial No. 2017-533728, Office Action dated Jan. 11, 2018", With English Translation, 9 pgs.

"Japanese Application Serial No. 2017-542797, Office Action dated May 21, 2018", with English translation, 4 pgs.

"Japanese Application Serial No. 2017-542797, Response filed Aug. 17, 2018 to Office Action dated May 21, 2018", w/ English claims, 9 pgs.

Moffitt, Michael A., et al., "Graphical User Interface for Programming Neurostimulation Pulse Patterns", U.S. Appl. No. 14/853,589, filed Sep. 14, 2015.

"U.S. Appl. No. 15/079,340, Non Final Office Action dated May 13, 2019", 13 pgs.

"U.S. Appl. No. 15/079,340, Supplemental Amendment and Response dated Apr. 10, 2019", 14 pgs.

"U.S. Appl. No. 15/290,776, Notice of Allowance dated Apr. 24, 2019", 8 pgs.

* cited by examiner

GRAPHICAL USER INTERFACE FOR PROGRAMMING NEUROSTIMULATION PULSE PATTERNS

CLAIM OF PRIORITY

This application is a continuation of U.S. application Ser. No. 14/853,589, filed Sep. 14, 2015, now issued as U.S. Pat. No. 9,737,717, which claims the benefit of priority under 35 U.S.C. § 119(e) of U.S. Provisional Patent Application Ser. No. 62/050,505, filed on Sep. 15, 2014, each of which is herein incorporated by reference in its entirety.

TECHNICAL FIELD

This document relates generally to neurostimulation and more particularly to a programming method and apparatus using a graphical user interface that allows a user to customize various patterns and waveforms of neurostimulation pulses.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform waveforms continuously or in bursts. However, the human nervous systems use neural signals having much more sophisticated patterns to communicate various types of information, including sensations of pain, pressure, temperature, etc. The nervous system may interpret an artificial stimulation with a simple pattern of stimuli as an unnatural phenomenon, and respond with an unintended and undesirable sensation and/or movement. For example, some neurostimulation therapies are known to cause paresthesia and/or vibration of non-targeted tissue or organ.

Recent research has shown that the efficacy and efficiency of certain neurostimulation therapies can be improved, and their side-effects can be reduced, by using patterns of neurostimulation pulses that emulate natural patterns of neural signals observed in the human body. While modern electronics can accommodate the need for generating such sophisticated pulse patterns, the capability of a neurostimulation system depends on its post-manufacturing programmability to a great extent. For example, a sophisticated pulse pattern may only benefit a patient when it is customized for that patient, and waveform patterns predetermined at the time of manufacturing may substantially limit the potential for the customization. In various applications, the customization may require pulse-by-pulse programmability and make the programming of the complete pulse pattern a challenging task. As such a task may be performed at least in part by a user such as a physician or other caregiver with the patient in a clinical setting, there is a need for an intuitive, user-friendly method and system for programming the neurostimulation pulse pattern.

SUMMARY

An example (e.g. "Example 1") of a system for delivering neurostimulation pulses through a plurality of electrodes may include a storage device, a programming control circuit, and a graphical user interface (GUI). The storage device may be configured to store a plurality of individually definable waveforms. The programming control circuit may be configured to generate a plurality of stimulation parameters controlling the delivery of the neurostimulation pulses according to a pattern of the neurostimulation pulses. The GUI is coupled to the storage device and the control circuit, and may be configured to define the pattern of the neurostimulation pulses using one or more waveforms selected from the plurality of individually definable waveforms. The GUI may be further configured to display waveform tags each selectable for access to a waveform of the plurality of individually definable waveforms, and display a waveform builder in response to selection of a waveform tag of the waveform tags. The waveform builder may be configured to present a graphical representation of the accessed waveform and allow for the accessed waveform to be adjusted by editing the graphical representation of the accessed waveform on the GUI.

In Example 2, the subject matter of Example 1 may optionally be configured such that the waveform tags include one or more waveform addition tags each selectable for adding a new waveform to the plurality of individually definable waveforms, and the waveform builder displayed in response to selection of a waveform addition tag of the one or more waveform addition tags allows for creation and editing of a graphical representation of the new waveform on the GUI.

In Example 3, the subject matter of any one or any combination of Examples 1 and 2 may optionally be configured such that the GUI is configured to display the graphical representation of the accessed waveform by visually indicating parameters defining the accessed waveform and allow user modification of one or more parameters of the visually indicated parameters defining the accessed waveform.

In Example 4, the subject matter of any one or any combination of Examples 1-3 may optionally be configured such that the GUI includes a touchscreen and is configured to display the graphical representation of the accessed waveform on the touchscreen and allow for the accessed waveform to be adjusted by editing the graphical representation on the touchscreen.

In Example 5, the subject matter of any one or any combination of Examples 1-4 may optionally be configured such that the GUI is configured to organize the stored plurality of individually definable waveforms into a hierarchical structure including a plurality of levels, and allow each waveform of each level of the plurality of levels to include one or more waveforms of one or more lower levels.

In Example 6, the subject matter of Example 5 may optionally be configured such that the GUI is configured to organize the stored plurality of individually definable waveforms into a nested hierarchical structure including a first level including one or more basic waveforms, a second level including one or more waveform groups each including one or more basic waveforms selected from the first level, and a third level including one or more groups of waveform groups each including one or more waveform groups selected from the second level.

In Example 7, the subject matter Example 6 may optionally be configured such that the one or more basic waveforms include one or more pulses of the neurostimulation pulses, the one or more pulses each being defined by a set of pulse parameters.

In Example 8, the subject matter of any one or any combination of Examples 6 and 7 may optionally be configured such that the storage device is further configured to store a plurality of individually definable fields each defined by one or more electrodes of the plurality of electrodes through which the pulse of a basic waveform of the one or more basic waveform is delivered. The GUI is further configured to display field tags each selectable for access to a field of the plurality of individually definable fields, and display a field builder in response to selection of a field tag of the field tags. The field builder is configured to present a graphical representation of the accessed field and allow for the accessed field to be adjusted by editing the graphical representation of the accessed field on the GUI. The field tags include one or more field addition tags each selectable for adding a new field to the plurality of individually definable waveforms. The field builder is displayed in response to selection of a field addition tag of the one or more field addition tags to allow for creation and editing of a graphical representation of the new field on the GUI.

In Example 9, the subject matter of any one or any combination of Examples 7 and 8 may optionally be configured such that the one or more waveform groups comprise one or more pulse groups (PGs) each being defined by a set of PG parameters specifying the one or more pulses selected from the stored one or more pulses and the timing of each pulse of the specified one or more pulses.

In Example 10, the subject matter of Example 9 may optionally be configured such that the one or more groups of waveform groups include one or more groups of pulse groups (GPGs) each defined by a set of GPG parameters specifying the one or more PGs selected from the stored one or more PGs and timing of each PG of the specified one or more PGs.

In Example 11, the subject matter of any one or any combination of Examples 5-10 may optionally be configured such that the GUI includes a plurality of display modes and a display mode input configured to receive selection of a display mode from the plurality of display modes, the display modes each specifying a level of detail to be displayed for each level of the hierarchical structure.

In Example 12, the subject matter of any one or any combination of Examples 1-11 may optionally be configured to further include a programmer and an implantable neurostimulator. The programmer includes the storage device, the control circuit, and the GUI. The implantable neurostimulator may be configured to be coupled to the plurality of electrodes and communicatively coupled to the programmer. The implantable neurostimulator includes a stimulation output circuit to produce and deliver each of the neurostimulation pulses through a set of electrodes selected from the plurality of electrodes and a stimulation control circuit to control the delivery of the neurostimulation pulses using the plurality of stimulation parameters specifying a pattern of the neurostimulation pulses.

In Example 13, the subject matter of any one or any combination of Examples 1-12 may optionally be configured such that the programming control circuit is configured to check the plurality of stimulation parameters against constraints of safety rules.

In Example 14, the subject matter of any one or any combination of Examples 1-13 may optionally be configured such that the GUI is configured to allow for export of a waveform of the plurality of individually definable waveforms from the system.

In Example 15, the subject matter of any one or any combination of Examples 1-14 may optionally be configured such that the GUI is configured to allow for import of a waveform into the system to be added to the plurality of individually definable waveforms.

An example of a method (e.g., "Example 16") for delivering neurostimulation pulses through a plurality of electrodes is also provided. The method includes storing a plurality of individually definable waveforms; defining a pattern of the neurostimulation pulses using a GUI, the pattern of the neurostimulation pulses including one or more waveforms selected from the stored plurality of individually definable waveforms; displaying waveform tags using the GUI, the waveform tags each selectable for access to a waveform of the plurality of individually definable waveforms; receiving from a user a selection of a waveform tag of the displayed waveform tags, the selected waveform tag associated with the accessed waveform; displaying a graphical representation of the accessed waveform using the GUI; and allowing for the accessed waveform to be adjusted by the user editing the graphical representation of the accessed waveform on the GUI.

In Example 17, the subject matter of Example 16 may optionally further include exporting a waveform of the plurality of individually definable waveforms for sharing with one or more other users.

In Example 18, the subject matter of any one or any combination of Examples 16 and 17 may optionally further include importing a waveform from another user to be added to the plurality of individually definable waveforms.

In Example 19, the subject matter of the waveform tags as found in any one or any combination of Examples 16-18 may optionally further include one or more waveform addition tags each selectable for adding a new waveform to the plurality of individually definable waveforms, and the subject matter of any one or any combination of Examples 16-18 may further include allowing the user to create and edit a graphical representation of the new waveform on the GUI.

In Example 20, the subject matter of displaying the graphical representation of the accessed waveform as found in any one or any combination of Examples 16-19 may optionally further include visually indicating parameters defining the accessed waveform on a touchscreen of the GUI, and the subject matter of allowing for the accessed waveform to be adjusted as found in any one or any combination of Examples 16-19 may optionally further include allowing for adjustment of one or more parameters of the parameters defining the accessed waveform by the user using the touchscreen.

In Example 21, the subject matter of any one or any combination of Examples 16-20 may further include organizing the stored plurality of individually definable waveforms into a hierarchical structure including a plurality of levels, and allowing each waveform of each level of the plurality of levels to include one or more waveforms of one or more lower levels.

In Example 22, the subject matter of storing the plurality of individually definable waveforms as found in Example 21 may optionally include storing one or more pulses of the neurostimulation pulses, the one or more pulses each being defined by a set of pulse parameters, storing one or more pulse groups (PGs) each being defined by a set of PG parameters specifying the one or more pulses selected from the stored one or more pulses and the timing of each pulse of the specified one or more pulses, and storing one or more groups of pulse groups (GPGs) each defined by a set of GPG parameters specifying the one or more PGs selected from the stored one or more PGs and timing of each PG of the specified one or more PGs.

In example 23, the subject matter of any one or any combination of Examples 16-22 may optionally further include storing a plurality of individually definable fields each defined by one or more electrodes selected from the plurality of electrodes and assigned to a pulse of the stored one or more pulses to be delivered through the one or more electrodes, displaying field tags using the GUI, the field tags each selectable for access to a field of the plurality of individually definable fields, receiving from the user a selection of a field tag of the displayed field tags, the selected field tag associated with the accessed field, displaying a graphical representation of the accessed field using the GUI, and allowing for the accessed field to be adjusted by the user editing the graphical representation of the accessed field on the GUI.

In Example 24, the subject matter of any one or any combination of Examples 16-23 may optionally further include transmitting the plurality of stimulation parameters to an implantable neurostimulator, delivering the neurostimulation pulses from the implantable neurostimulator, and controlling the delivery of the neurostimulation pulses using the plurality of stimulation parameters transmitted to the implantable neurostimulator.

In Example 25, the subject matter of Example 24 may optionally further include checking the plurality of stimulation parameters against constraints of safety rules before transmitting the plurality of stimulation parameters to the implantable neurostimulator.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a method and system for programming neurostimulation pulse patterns using a graphical user interface (GUI). Advancements in neuroscience and neurostimulation research have led to a demand for using complex and/or individually optimized patterns of neurostimulation pulses for various types of therapies. The capability of a neurostimulation system in treating various types of disorders will be limited by the programmability of such patterns of neurostimulation pulses. In various embodiments, the present system allows for custom definition of a pattern of neurostimulation pulses, which includes custom definition of waveforms being the building blocks of the pattern Such custom definition is achieved by using a GUI that makes it possible for the user to perform the custom definition of potentially very complex patterns of neurostimulation pulses by creating and editing graphical representations of relatively simple individual building blocks for each of the patterns. In various embodiments, the individually definable waveforms may include pulses, pulse groups each including different pulses each timed in a sequence with controllable duty cycle, and groups of pulse groups each including different pulse groups each timed in a sequence with controllable duty cycle. In various embodiments, the present system provides for patterns of neurostimulation pulses not limited to waveforms predefined at the time of manufacturing, thereby accommodating need for customization of neurostimulation pulse patterns as well as need for new types of neurostimulation pulse patterns that may, for example, result from future research in neurostimulation. This may also facilitate design of a general-purpose neurostimulation device that can be configured by a user for delivering specific types of neurostimulation therapies by programming the device using the GUI.

Figure 1:
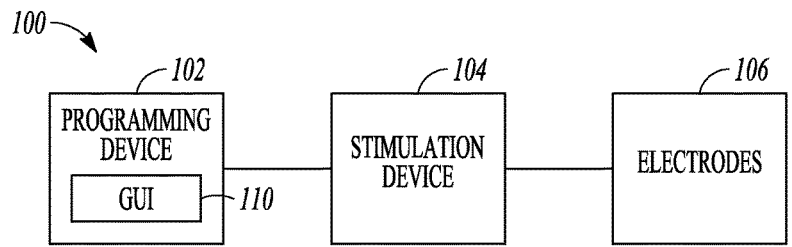
FIG. 1 illustrates an embodiment of a neurostimulation system.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In various embodiments, programming device 102 includes a graphical user interface (GUI) that allows the user to set and/or adjust values of the user-programmable parameters by creating and/or editing graphical representations of various waveforms. Such waveforms may include, for example, the waveform of a pattern of neurostimulation pulses to be delivered to the patient as well as individual waveforms that are used as building blocks of the pattern of neurostimulation pulses. Examples of such individual waveforms include pulses, pulse groups, and groups of pulse groups, as further discussed below. The user may also be allowed to define an electrode selection specific to each individually defined waveform.

Figure 2:
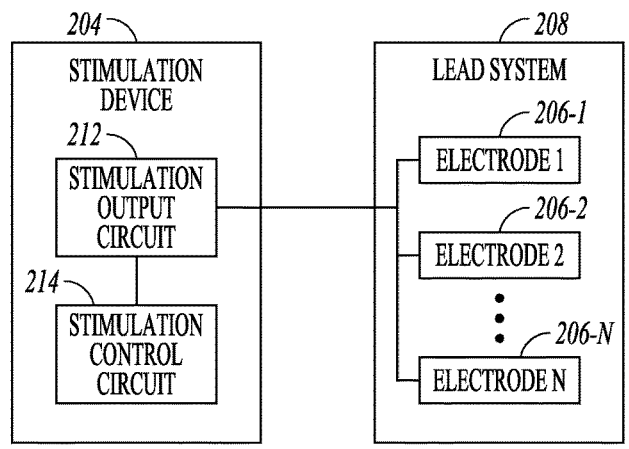
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an embodiment of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses.

In various embodiments, the number of leads and the number of electrodes on each lead depend on, for example, the distribution of target(s) of the neurostimulation and the need for controlling the distribution of electric field at each target. In various embodiments, which are illustrated in each of FIGS. 15-23 as examples for discussion of programming though the GUI, lead system includes 2 leads each having 8 electrodes.

Figure 3:
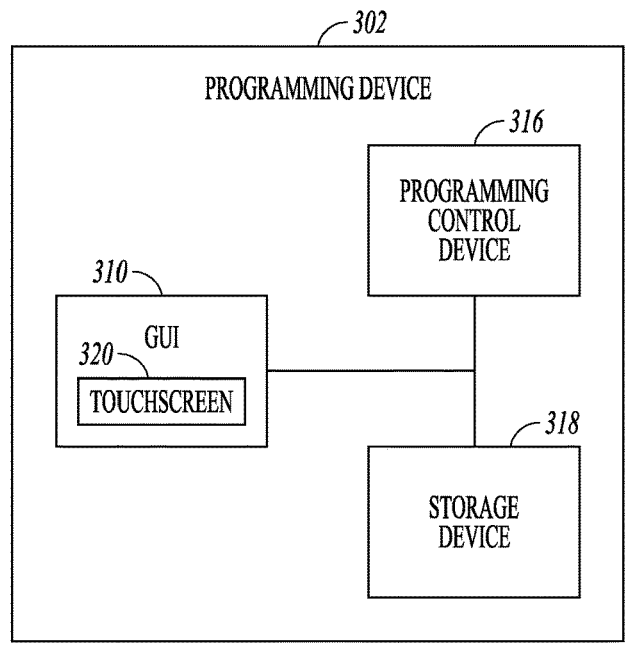
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a GUI 310. Storage device 318 stores a plurality of individually definable waveforms. Programming control circuit 316 generates the plurality of stimulation parameters that controls the delivery of the neurostimulation pulses according to the pattern of the neurostimulation pulses. GUI 310 represents an embodiment of GUI 110 and allows the user to define the pattern of the neurostimulation pulses using one or more waveforms selected from the plurality of individually definable waveforms. In various embodiments, GUI 310 is configured to display waveform tags each selectable for access to a waveform of the plurality of individually definable waveforms, and configured to display a waveform builder in response to selection of a waveform tag of the waveform tags. The waveform builder is configured to present a graphical representation of the accessed waveform and allow for the accessed waveform to be adjusted by editing the graphical representation of the accessed waveform using GUI 310.

In the illustrated embodiment, GUI 310 includes a touchscreen 320 to allow the user to edit the graphical representation of the accessed waveform using a finger or stylet. In various embodiments, GUI 310 includes any type of presentation device, such as interactive or non-interactive screens, and any type of user input devices that allow the user to edit the graphical representation of the accessed waveform, such as touchscreen, keyboard, keypad, touchpad, trackball, joystick, and mouse. In one embodiment, GUI 310 displays the graphical representation of the accessed waveform by visually indicating parameters defining the accessed waveform on touchscreen 320 and allows the user to modify one or more parameters of the visually indicated parameters using touchscreen 320, such as by dragging one or more segments of the accessed waveform.

In various embodiments, circuits of neurostimulation 100, including its various embodiments discussed in this document, may be implemented using a combination of hardware and software. For example, the circuit of GUI 100, stimulation control circuit 214, and programming control circuit 315, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
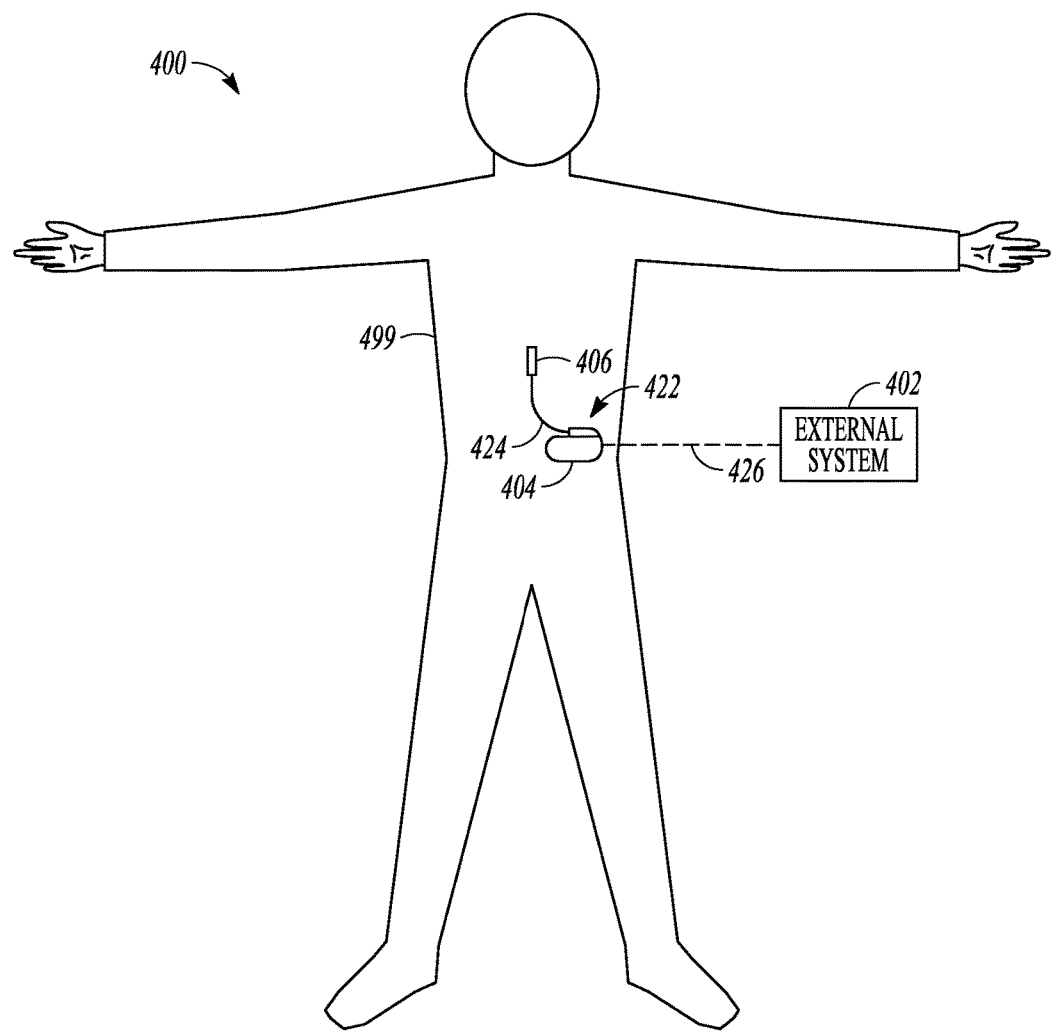
FIG. 4 illustrates an implantable neurostimulation system and portions of an environment in which the system may be used.

FIG. 4 illustrates an implantable neurostimulation system 400 and portions of an environment in which system 400 may be used. System 400 includes an implantable system 422, an external system 402, and a telemetry link 426 providing for wireless communication between implantable system 422 and external system 402. Implantable system 422 is illustrated in FIG. 4 as being implanted in the patient's body 499.

Implantable system 422 includes an implantable stimulator (also referred to as an implantable pulse generator, or IPG) 404, a lead system 424, and electrodes 406, which represent an embodiment of stimulation device 204, lead system 208, and electrodes 206, respectively. External system 402 represents an embodiment of programming device 302. In various embodiments, external system 402 includes one or more external (non-implantable) devices each allowing the user and/or the patient to communicate with implantable system 422. In some embodiments, external 402 includes a programming device intended for the user to initialize and adjust settings for implantable stimulator 404 and a remote control device intended for use by the patient. For example, the remote control device may allow the patient to turn implantable stimulator 404 on and off and/or adjust certain patient-programmable parameters of the plurality of stimulation parameters.

Figure 5:
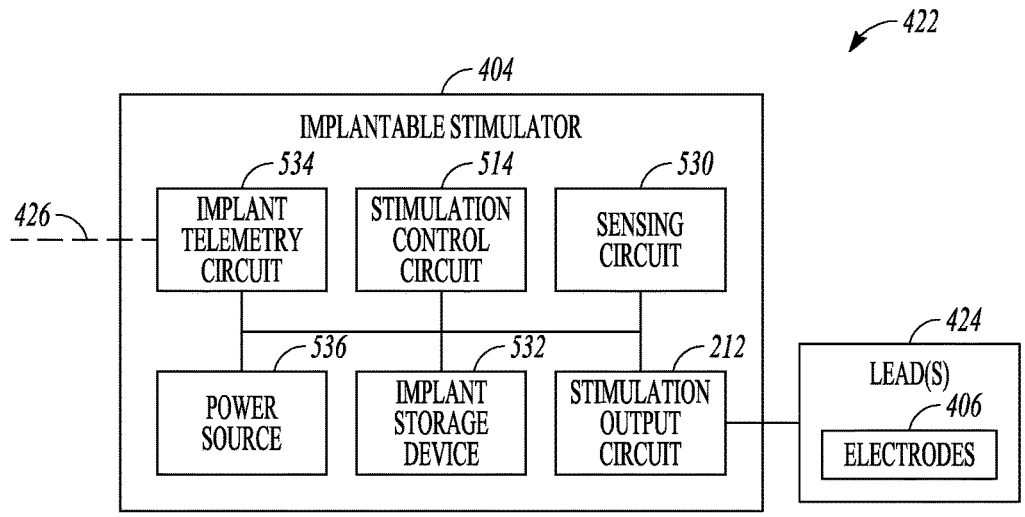
FIG. 5 illustrates an embodiment of an implantable stimulator and one or more leads of an implantable neurostimulation system, such as the implantable system of FIG. 4.

FIG. 5 illustrates an embodiment of implantable stimulator 404 and one or more leads 424 of an implantable neurostimulation system, such as implantable system 422. Implantable stimulator 404 may include a sensing circuit 530 that is optional and required only when the stimulator has a sensing capability, stimulation output circuit 212, a stimulation control circuit 514, an implant storage device 532, an implant telemetry circuit 534, and a power source 536. Sensing circuit 530, when included and needed, senses one or more physiological signals for purposes of patient monitoring and/or feedback control of the neurostimulation. Examples of the one or more physiological signals includes neural and other signals each indicative of a condition of the patient that is treated by the neurostimulation and/or a response of the patient to the delivery of the neurostimulation. Stimulation output circuit 212 is electrically connected to electrodes 406 through lead 424, and delivers each of the neurostimulation pulses through a set of electrodes selected from electrodes 406. Stimulation control circuit 514 represents an embodiment of stimulation control circuit 214 and controls the delivery of the neurostimulation pulses using the plurality of stimulation parameters specifying the pattern of the neurostimulation pulses. In one embodiment, stimulation control circuit 514 controls the delivery of the neurostimulation pulses using the one or more sensed physiological signals. Implant telemetry circuit 534 provides implantable stimulator 404 with wireless communication with another device such as a device of external system 402, including receiving values of the plurality of stimulation parameters from external system 402. Implant storage device 532 stores values of the plurality of stimulation parameters. Power source 536 provides implantable stimulator 404 with energy for its operation. In one embodiment, power source 536 includes a battery. In one embodiment, power source 536 includes a rechargeable battery and a battery charging circuit for charging the rechargeable battery. Implant telemetry circuit 534 may also function as a power receiver that receives power transmitted from external system 402 through an inductive couple.

In various embodiments, sensing circuit 530 (if included), stimulation output circuit 212, stimulation control circuit 514, implant telemetry circuit 534, implant storage device 532, and power source 536 are encapsulated in a hermetically sealed implantable housing. In various embodiments, lead(s) 424 are implanted such that electrodes 406 are places on and/or around one or more targets to which the neurostimulation pulses are to be delivered, while implantable stimulator 404 is subcutaneously implanted and connected to lead(s) 424 at the time of implantation.

Figure 6:
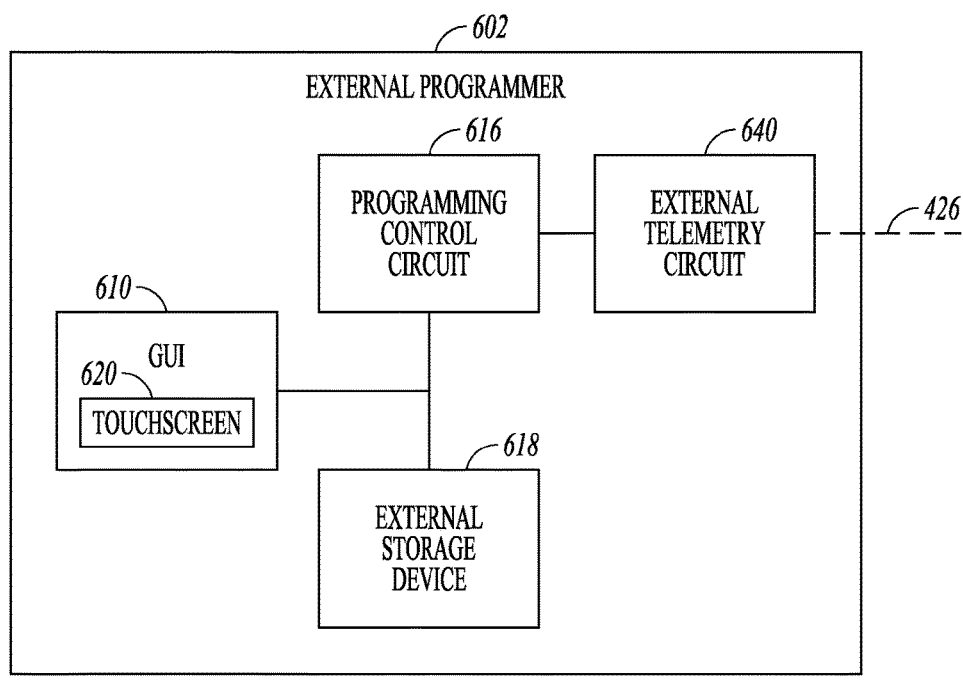
FIG. 6 illustrates an embodiment of an external programmer of an implantable neurostimulation system, such as the external system of FIG. 4.

FIG. 6 illustrates an embodiment of an external programmer 602 of an implantable neurostimulation system, such as external system 402. External programmer 602 represents an embodiment of programming device 302, and includes an external telemetry circuit 640, an external storage device 618, a programming control circuit 616, and a GUI 610.

External telemetry circuit 640 provides external programmer 602 with wireless communication with another device such as implantable stimulator 404 via telemetry link 426, including transmitting the plurality of stimulation parameters to implantable stimulator 404. In one embodiment, external telemetry circuit 640 also transmits power to implantable stimulator 404 through the inductive couple.

External storage device 618 stores a plurality of individually definable waveforms each selectable for use as a portion of the pattern of the neurostimulation pulses. In various embodiments, each waveform of the plurality of individually definable waveforms includes one or more pulses of the neurostimulation pulses, and may include one or more other waveforms of the plurality of individually definable waveforms. Examples of the waveforms are discussed below with reference to FIGS. 7 and 8. External storage device 618 also stores a plurality of individually definable fields. Each waveform of the plurality of individually definable waveforms is associated with one or more fields of the plurality of individually definable fields. Each field of the plurality of individually definable fields is defined by one or more electrodes of the plurality of electrodes through which a pulse of the neurostimulation pulses is delivered and a current distribution of the pulse over the one or more electrodes.

Programming control circuit 616 represents an embodiment of programming control circuit 316 and generates the plurality of stimulation parameters, which is to be transmitted to implantable stimulator 404, based on the pattern of the neurostimulation pulses. The pattern is defined using one or more waveforms selected from the plurality of individually definable waveforms stored in external storage device 618. In various embodiment, programming control circuit 616 checks values of the plurality of stimulation parameters against safety rules to limit these values within constraints of the safety rules. In one embodiment, the safety rules are heuristic rules.

GUI 610 represents an embodiment of GUI 310 and allows the user to define the pattern of the neurostimulation pulses using the one or more waveforms selected from the plurality of individually definable waveforms stored in external storage device 618, add new waveforms to the stored plurality of individually definable waveforms, and modify waveforms of the stored plurality of individually definable waveforms. In the illustrated embodiment, GUI 610 includes a touchscreen 620 to allow the user to edit graphical representations of the pattern of the neurostimulation pulses and the waveforms on the screen. In various embodiments, GUI 610 includes any types of presentation and user input devices that are suitable for used by the user to define and modify the pattern of the neurostimulation pulses and the waveforms.

In various embodiments, GUI 610 displays waveform tags each selectable for adding a new waveform to the plurality of individually definable waveforms stored in external storage device 618 or for adjusting a waveform of the plurality of individually definable waveforms stored in external storage device 618. The waveform tags may each be presented as a button, a tab, or another symbol identifying a waveform. In response to a waveform tag of the waveform tags being selected, GUI 610 displays a waveform builder. The waveform builder includes a graphical representation of a waveform that is adjustable by editing the graphical representation. The adjustable waveform is the new waveform to be added or the stored waveform to be adjusted. The editing may include, for example, modifying, deleting, copying, and repeating a portion of the graphical representation. In various embodiments, GUI 610 allows the user to edit the graphical representation of the waveform using textual and/or graphical commands. In various embodiments, GUI 610 allows the user to edit the graphical representation of the waveform by directly manipulating the graphical representation, such as on touchscreen 620. In various embodiments, the graphical representation of the waveform visually indicates parameters defining the waveform, including amplitude and timing parameters. In one embodiment, all the parameters defining the waveform are adjustable by the user using GUI 610. In various embodiments, the parameters defining the waveform include a field parameter specifying a field assigned to the waveform. The field parameter specifies one or more electrodes and a current distribution over the one or more electrodes.

In various embodiments, GUI 610 displays field tags each selectable for adding a new field to the plurality of individually definable fields stored in external storage device 618 or adjusting a field of the plurality of individually definable fields stored in external storage device 618. The field tags may each be presented as a button, a tab, or other symbol identifying a field. In response to a field tag of the waveform tags being selected, GUI 610 displays a field builder. The field builder includes a graphical representation of a field that is adjustable by editing the graphical representation. The adjustable field is represented by one or more electrodes selected from the plurality of electrodes 406 and the current distribution over the selected one or more electrodes. The adjustable field is the new field to be added or the stored field to be adjusted. The current distribution may be specified by a percentage associated with each electrode of the selected one or more electrodes. In various embodiments, each field of the stored plurality of individually definable fields may be assigned to a waveform of the stored plurality of individually definable waveforms or a portion of that waveform. In various embodiments, visual tags, such as various colors and/or text, are applied to associate a field with a waveform or a portion of the waveform to which the field is assigned to.

In various embodiments, GUI 610 allows for export of a waveform of the plurality of individually definable waveforms stored in external storage device 618 from external programmer 602. In various embodiments, GUI 610 allows for import of a waveform into external programmer 602 to be added to the plurality of individually definable waveforms stored in external storage device 618. In various embodiments, GUI 610 allows for export of a field of the plurality of individually definable fields stored in external storage device 618 from external programmer 602. In various embodiments, GUI 610 allows for import of a field into external programmer 602 to be added to the plurality of individually definable fields stored in external storage device 618. In one embodiment, such import and export are performed via the Internet or cloud, in a forum for sharing waveforms. Such imports and exports enable the user to share waveforms and/or fields with other users in a community of users that use the same or similar neurostimulation systems to treat patients.

Figure 7:
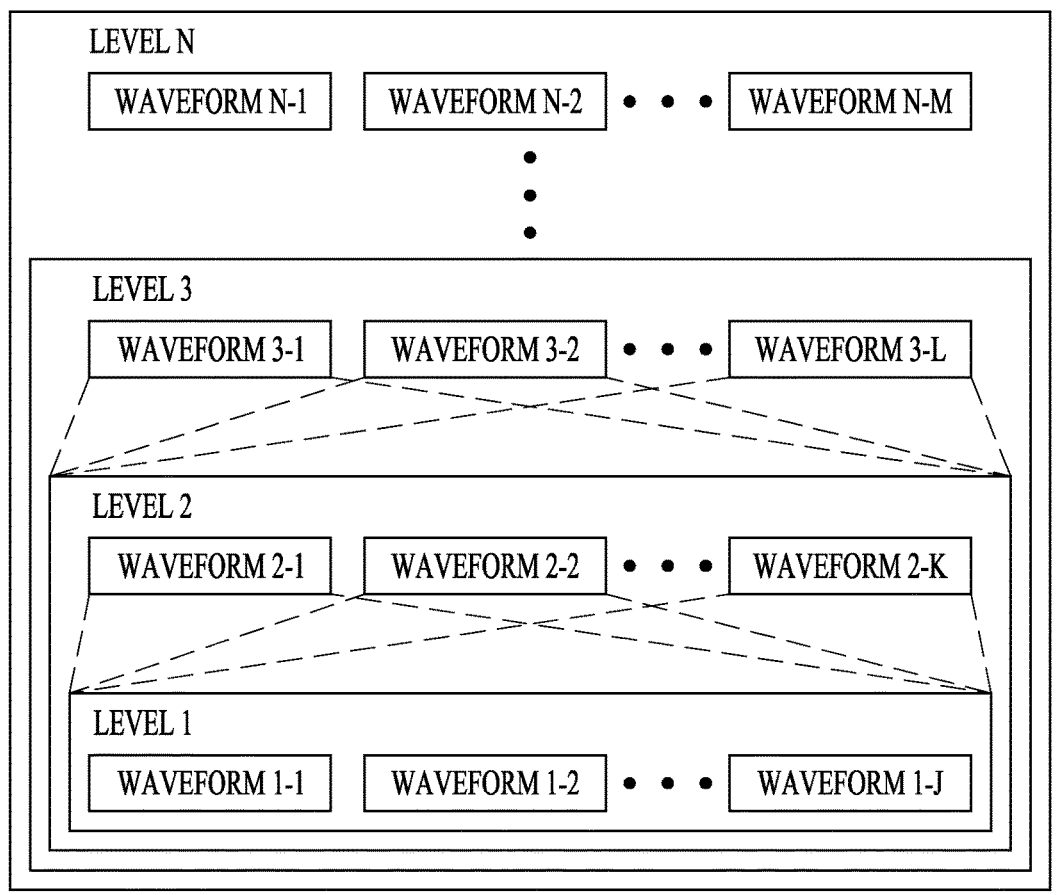
FIG. 7 is an illustration of an embodiment of waveforms of neurostimulation organized in a hierarchical structure.

FIG. 7 is an illustration of an embodiment of waveforms of neurostimulation organized in a hierarchical structure. The waveforms may include, for example, the waveform of a pattern of neurostimulation pulses to be delivered to the patient as well as individual waveforms that are used as building blocks of the pattern of neurostimulation pulses. In one embodiment, waveforms of the plurality of individually definable waveforms stored in external storage device 618 are organized into such a hierarchical structure, which includes a plurality of levels (layers). A waveform of each level includes one or more waveforms of one or more lower levels.

In the illustrated embodiment, the waveforms of the plurality of individually definable waveforms stored in external storage device 618 are organized into a nested hierarchical structure with N levels, where N≥2. Level 1 includes one or more waveforms (waveform 1-1, waveform 1-2, . . . waveform 1-J, where J≥1). Level 2 includes one or more waveforms (waveform 2-1, waveform 2-2, . . . waveform 2-K, where K≥1) each including one or more of waveforms selected from Level 1. Level 3 includes one or more waveforms (waveform 3-1, waveform 3-2, . . . waveform 3-L, where L≥1) each including one or more of waveforms selected from Level 2. In general, Level N includes one or more waveforms (waveform N-1, waveform N-2, . . . waveform 2-M, where M≥1) each including one or more of waveforms selected from Level N-1. The one or more waveforms of Level N-1 may be selected multiple times for inclusion in a waveform of Level N.

In one example, the waveforms of the plurality of individually definable waveforms stored in external storage device 618 are organized into a nested hierarchical structure with three levels (N=3). Level 1 includes one or more basic waveforms. Level 2 includes one or more waveform groups each including one or more basic waveforms selected from Level 1. Level 3 includes one or more groups of waveform groups each including one or more waveform groups selected from Level 2. In one embodiment, the pattern of neurostimulation pulses includes one or more waveforms selected from the one or more groups of waveform groups of Level 3. In various embodiments, the pattern of neurostimulation pulses may include any combination of waveforms from any one, two, or three levels as determined by the user.

Figure 8:
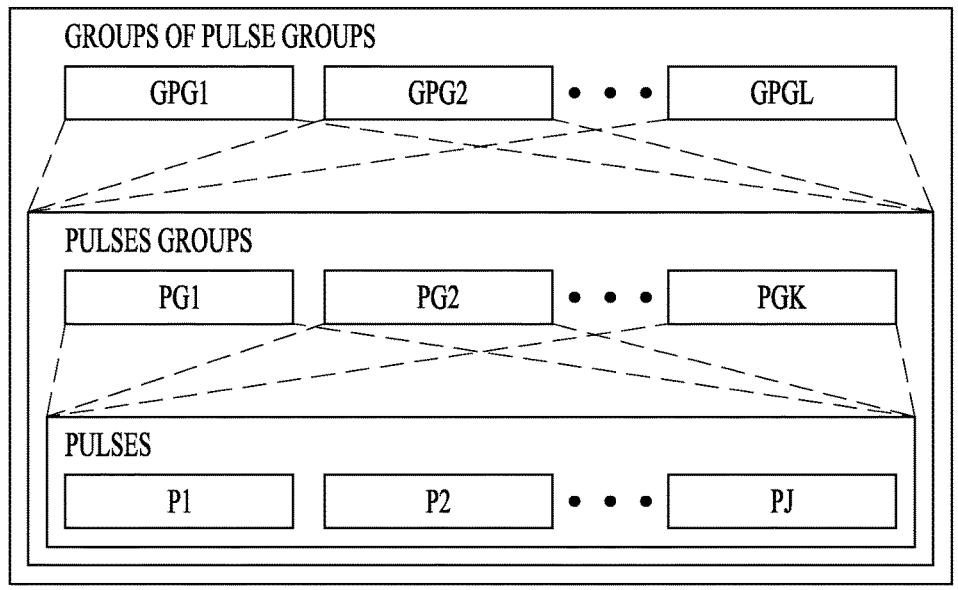
FIG. 8 illustrates a more specific embodiment of the waveforms of FIG. 7.

FIG. 8 illustrates a more specific embodiment of the waveforms of FIG. 7. In the illustrated embodiment, the waveforms of the plurality of individually definable waveforms stored in external storage device 618 are organized into a nested hierarchical structure with three levels (N=3).

Figure 9:
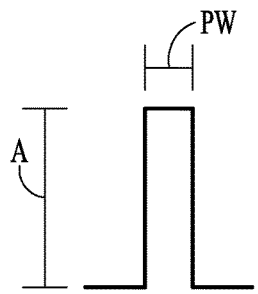
FIG. 9 illustrates an embodiment of a neurostimulation pulse.

Level 1 includes one or more pulses (P1, P2, ... PJ, where J≥1) each being independently defined by a set of pulse parameters. The set of pulse parameters specify a field of the stored plurality of individually definable fields, amplitude, shape, and timing of each pulse of the one or more pulses. FIG. 9 illustrates an embodiment of a neurostimulation pulse being a monophasic pulse having an amplitude (A) and a pulse width (PW). The monophasic pulse is used for easy illustration of waveforms of higher level, while the one or more pulses of Level 1 may each include any pulse waveform that is suitable for neurostimulation. In various embodiments, the neurostimulation pulses may each have a square, rectangular, or other waveforms including those with arbitrary shapes as defined by the user.

Figure 10:
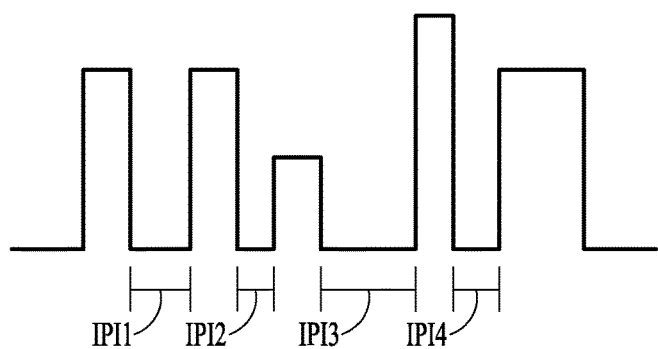
FIG. 10 illustrates an embodiment of a pulse group (PG).

Level 2 includes one or more pulse groups (PG1, PG2, PGK, where K≥1) each being independently defined by a set of PG parameters. The one or more PGs each include one or more pulses selected from the one or more pulses of Level 1. The set of PG parameters specifies the one or more pulses and the timing of each pulse of the one or more pulses. FIG. 10 illustrates an embodiment of a PG. In the illustrated embodiment, timing of each pulse is specified using an inter-pulse interval (WI), which is the time interval between two adjacent pulses.

Figure 11A:
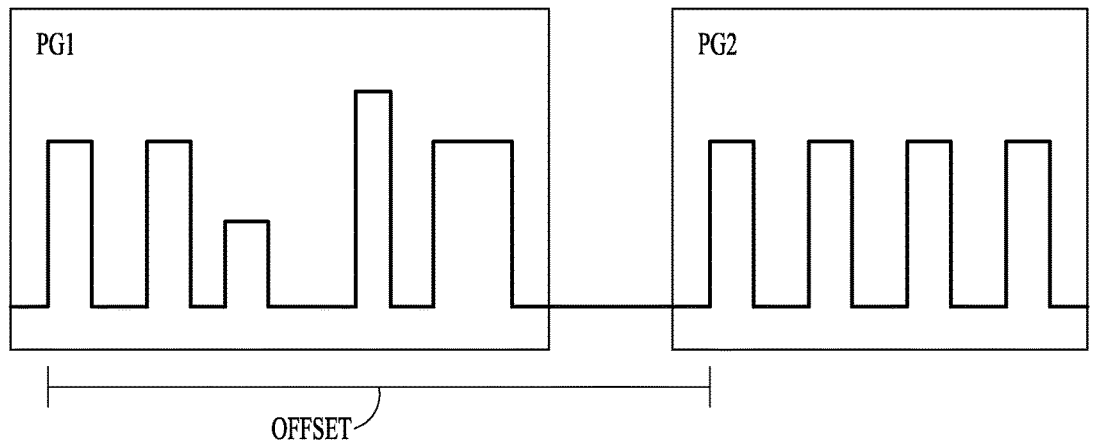
FIGS. 11A and 11B each illustrate an embodiment of a group of pulse groups (GPG).
Figure 11B:
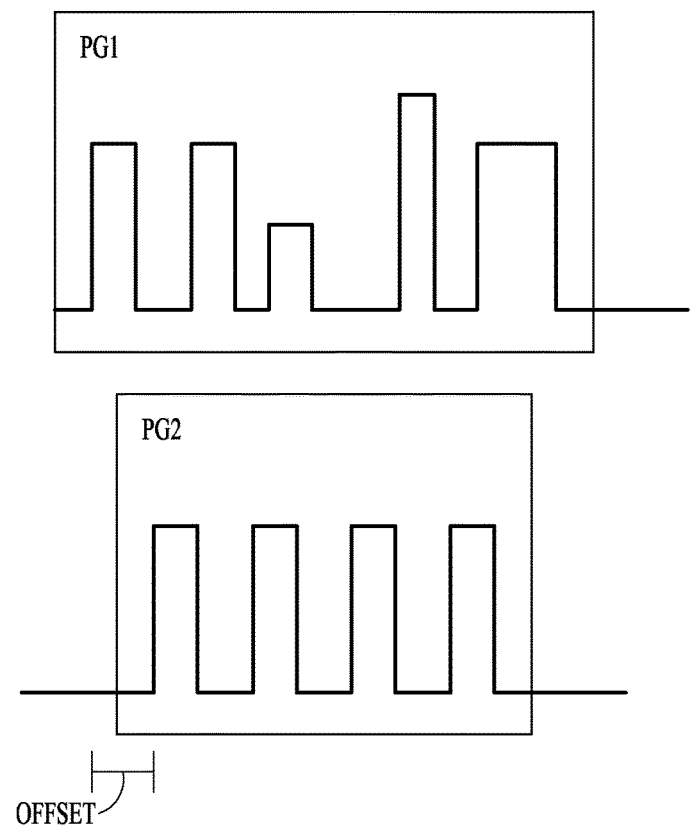

Level 3 includes one or more groups of pulse groups (GPG1, GPG2, GPGL, where L≥1) each independently defined by a set of GPG parameters. The one or more GPGs each include one or more PGs selected from the one or more PGs of Level 2. The set of GPG parameters specifies the one or more PGs and timing of each PG of the one or more PGs. FIGS. 11A and 11B each illustrate an embodiment of a GPG. Timing of each PG is specified using an offset, which is the time interval between the beginning of that PG and the beginning of the GPG (or the beginning of the first PG in the GPG). In the embodiment illustrated in FIG. 11A, the PGs are delivered in series from one or more stimulation output channels, with the offset being set to avoid overlapping of pulses in time. In the embodiment illustrated in FIG. 11B, the PGs may be delivered in parallel from a plurality of stimulation output channels, and the offset can be set to as short as zero for a simultaneous delivery of the PGs.

Figure 12:
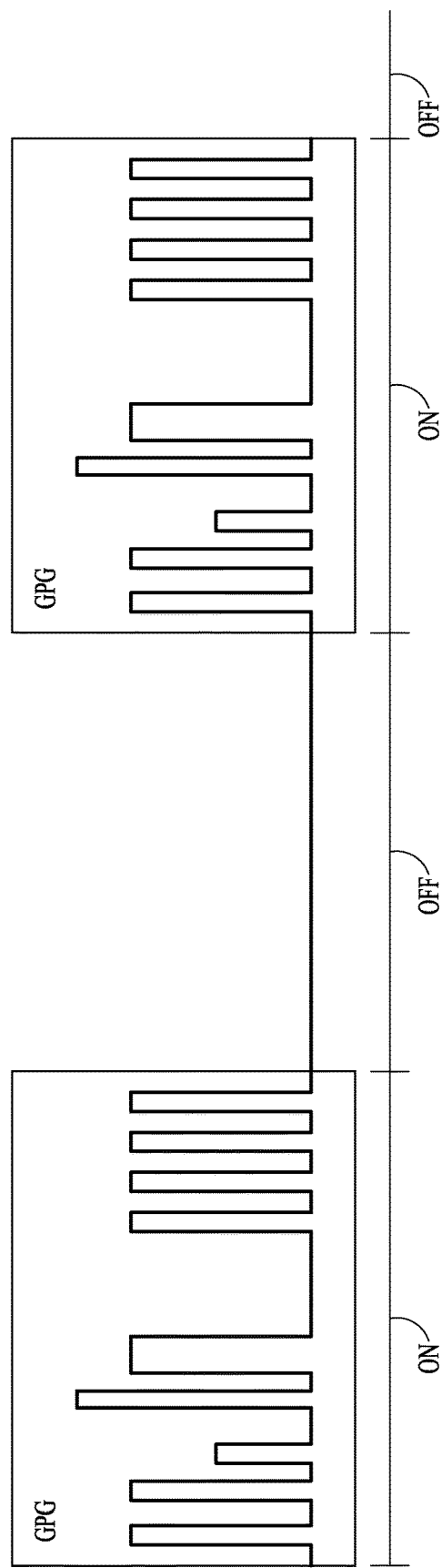
FIG. 12 illustrates an embodiment of a pattern of stimulation pulses.

In one embodiment, the pattern of neurostimulation pulses includes one or more waveforms selected from the one or more GPGs of Level 3. That is, the pattern of neurostimulation pulses includes one or more GPGs selected from the stored one or more GPGs, the stored one or more GPSs each includes one or more PGs selected from the stored one or more PGs, and the stored one or more PGs each including one or more pulses selected from the stored one or more pulses. FIG. 12 illustrates an embodiment of a pattern of stimulation pulses that includes a GPG repeated periodically with an OFF period during which no neurostimulation pulse is delivered. In various embodiments, the pattern of neurostimulation pulses may include any combination of pulses, PGs, and GPGs as determined by the user.

In various embodiments, GUI 610 can operate in a plurality of display modes each specifying one or more waveforms of the plurality of individually definable waveforms to be displayed. In one embodiment, GUI 610 may display a mode input to receive selection of a display mode from the user. For example, only a waveform selected by the user is displayed in detail according to one of the display modes, and one or more waveforms of a level in the hierarchical structure selected by the user may be displayed in detail according to another one of the display modes.

In various embodiments, GUI 610 can be configured to allow for scaling the amplitude and time dimensions of a PG (where all pulses within the PG are scaled). Scaling of amplitude can be done incrementally, so that the user can experience it in an incrementally increasing way. Scaling of time can also be done incrementally. In one embodiment, scaling of time can be done while holding the pulse shape constant (i.e., only inter-pulse intervals are increased/decreased).

In various embodiments, GUI 610 can be configured to allow for saving, loading, exporting, and importing PGs and GPGs. This allows sharing of useful waveforms and patterns of the neurostimulation with other users in a community of users.

In various embodiments, GUI 610 can be configured to allow for programming a duty cycle for each level in the hierarchical structure. In various embodiments, GUI 610 can be configured to allow for testing of a given pulse design in a "tonic" mode that allows the user to adjust amplitude and otherwise characterize the pulse. Similarly, GUI 610 can be configured to support testing of a PG or GPG in a tonic mode. In various embodiments, the pulse, PG, or GPG are continuously delivered, without the OFF period.

Figure 13:
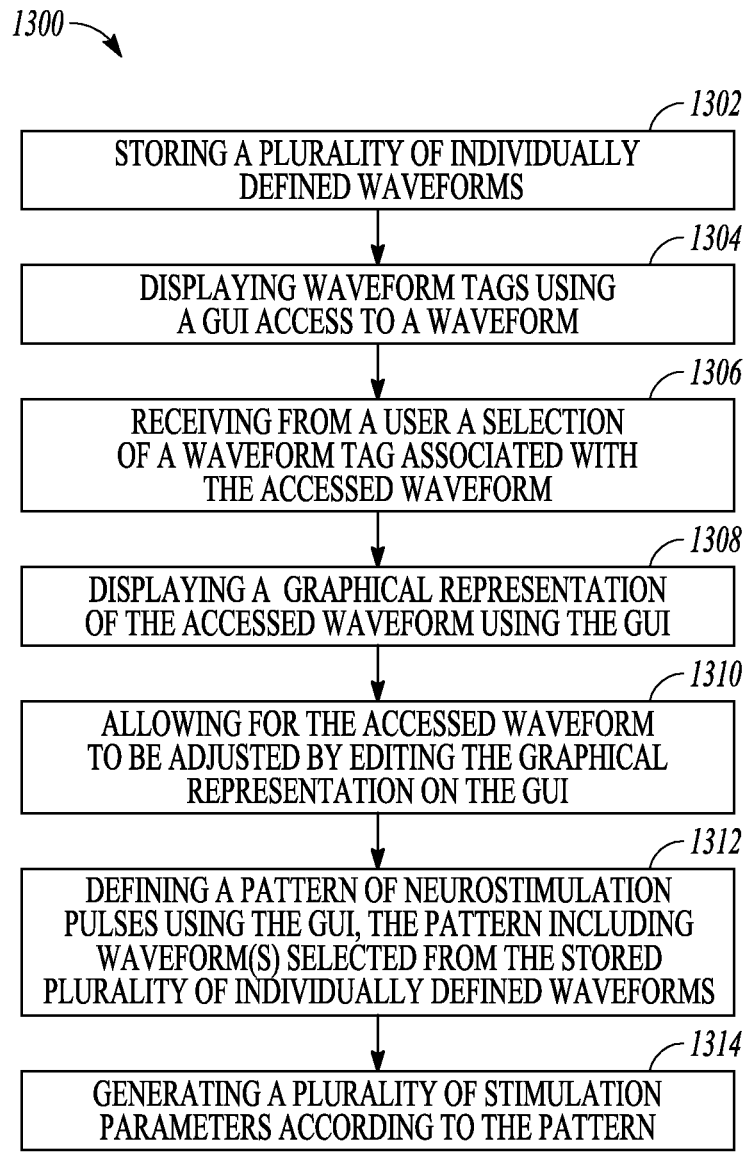
FIG. 13 illustrates an embodiment of a method for controlling delivery of neurostimulation pulses.

FIG. 13 illustrates an embodiment of a method 1300 for controlling delivery of neurostimulation pulses through a plurality of electrodes. In one embodiment, method 1300 is performed using system 100, including the various embodiments of its elements as discussed in this document. In various embodiments, programming device 102, programming device 302, and external programmer 602 may each be programmed to perform method 1300.

At 1302, a plurality of individually definable waveforms is stored. In various embodiments, the stored plurality of individually definable waveforms is organized into a hierarchical structure including a plurality of levels. Each waveform of each level of the plurality of levels can include one or more waveforms of one or more lower levels. In various embodiments, the stored plurality of individually definable waveforms may include one or more pulses of the neurostimulation pulses, one or more pulse groups (PGs), and one or more groups of pulse groups (GPGs). The one or more pulses are each defined by a set of pulse parameters. The one or more PGs are each defined by a set of PG parameters specifying the one or more pulses selected from the stored one or more pulses and the timing of each pulse of the specified one or more pulses. The one or more GPGs are each defined by a set of GPG parameters specifying the one or more PGs selected from the stored one or more PGs and timing of each PG of the specified one or more PGs. In various embodiments, a plurality of individually definable fields is also stored. The fields are each defined by one or more electrodes selected from the plurality of electrodes and a current distribution over the selected one or more electrodes, and assigned to a pulse of the stored one or more pulses to be delivered through the selected one or more electrodes.

At 1304, waveform tags are displayed using a GUI. The waveform tags are each selectable for access to a waveform of the plurality of individually definable waveforms. At 1306, a selection of a waveform tag from the displayed waveform tags is received from a user such as a physician or other caregiver. The selected waveform tag is associated with the accessed waveform. At 1308, a graphical representation of the accessed waveform is displayed using the GUI. At 1310, the user is allowed to adjust the accessed waveform by editing the graphical representation of the accessed waveform using the GUI.

In various embodiments, the waveform tags include one or more waveform addition tags each selectable for adding a new waveform to the plurality of individually definable waveforms. By selecting a waveform addition tag, the user is allowed user to create and edit a graphical representation of the new waveform on the GUI. In various embodiments, the graphical representation of the accessed waveform is displayed, with parameters defining the accessed waveform visually indicated, using the GUI, such as on a touchscreen of the GUI. The user is allowed to adjust one or more parameters of the parameters defining the accessed waveform, such as by using the touchscreen.

In various embodiments, field tags are displayed using the GUI. The field tags are each selectable for access to a field of the plurality of individually definable fields. A selection of a field tag of the displayed field tags is received from the user. The selected field tag is associated with the accessed field. A graphical representation of the accessed field is displayed using the GUI. The user can adjust the accessed field by editing the graphical representation of the accessed field on the GUI.

At 1312, a pattern of neurostimulation pulses is defined by using the GUI. The pattern of neurostimulation pulses includes one or more waveforms selected from the stored plurality of individually definable waveforms. At 1314, a plurality of stimulation parameters controlling the delivery of the neurostimulation pulses is generated according to the pattern of the neurostimulation pulses. The plurality of stimulation parameters is transmitted to a stimulation device such as an implantable stimulator for controlling the delivery of the neurostimulation pulses from the stimulation device. In various embodiments, values of the plurality of stimulation parameters are checked against constraints of safety rules before the plurality of stimulation parameters is transmitted to the stimulation device.

Figure 14:
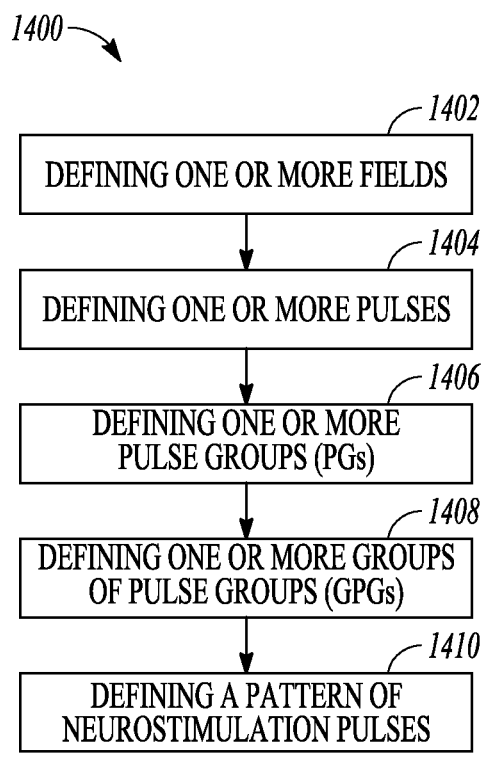
FIG. 14 illustrates an embodiment of a method for waveform building.

FIG. 14 illustrates an embodiment of a method 1400 for waveform building. In one embodiment, method 1400 is performed using system 100, including the various embodiments of its elements discussed in this document. In various embodiments, programming device 102, programming device 302, and external programmer 602 may each be programmed to perform method 1400. FIGS. 15-23 illustrate examples of a screen, such as a touchscreen, of the GUI configured for performing method 1400. Examples of the GUI include any GUI discussed in this document, including GUI 110, 310, and 610. For the purpose of illustration, a first lead 1524A including electrodes E1-E8, a second lead 1524B including electrodes E9-E16, and a case 1507 are shown as part of an implantable system being programmed using the GUI. Case 1507 includes at least a portion of an implantable housing used as an electrode. Electrode E2 is selected as a cathode to which 100% of the cathodic current is allocated. Electrode E1 is selected as an anode to which 25% of the anodic current has is allocated. Electrode E3 is selected as another anode to which 75% of the anodic current is allocated. Electrode E15 is selected to allow the user to subsequently allocate the polarity and fractionalized electrical current to it. The specific numbers, the features of the GUI, and the system being programmed are shown in 15-23 by way of example, and not by way of restriction, for the purpose of illustrating the functions of the GUIs as discussed in this document.

Figure 15:
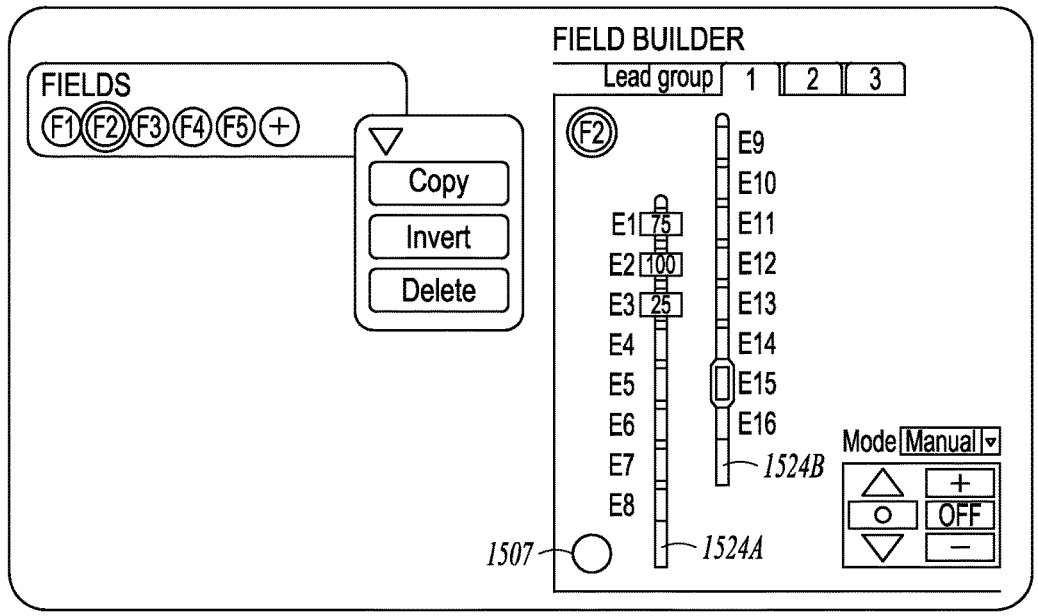
FIG. 15 is an illustration of an embodiment of a screen of a graphical user interface (GUI) for building a field.

At 1402, one or more fields are defined. Each field of the one or more fields is defined by one or more electrodes through which a pulse of the neurostimulation pulses is delivered and a current distribution of the pulse over the one or more electrodes. FIG. 15 is an illustration of an embodiment of the screen for building a field. The screen displays field tags F1-F5 indicating that 5 fields are stored and a new field tag "+" allowing the user to define a new field and add it to the stored fields. In the example as illustrated, in response to the field tag F2 being selected, the GUI displays a field builder that includes a graphical representation of the field F2. The user is allowed to modify electrode selection and allocation of current to each of the selected electrodes. The GUI provides a command menu providing the user with field editing options. Examples of the commands, as illustrated in FIG. 15, include "Copy" (which allows the user to copy a defined field and paste to another field as a template, for example), "Invert" (which allows the user to change the polarity of the waveform, i.e., swap the anode(s) and cathode(s)), and "Delete" (which allows the user to delete a defined field, i.e., remove it from the stored fields).

Figure 16:
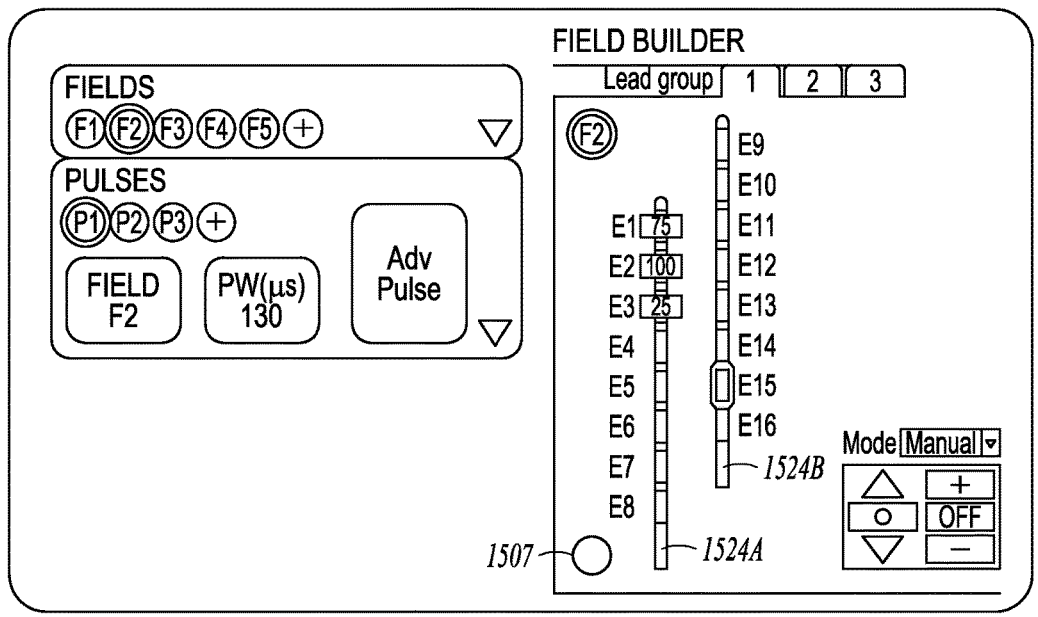
FIG. 16 illustrates an embodiment of the screen for building a pulse.
Figure 17:
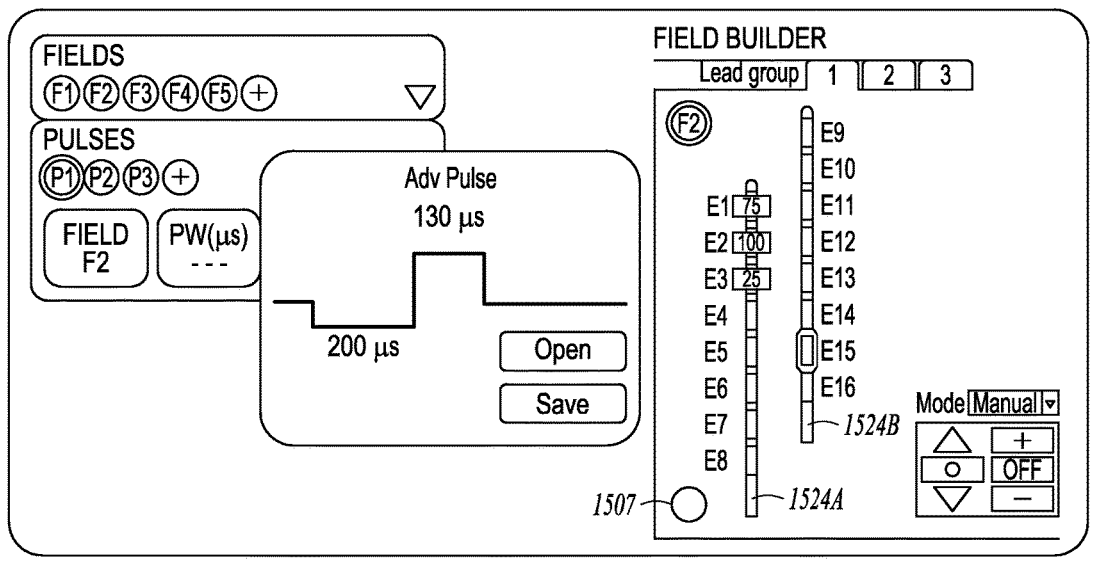
FIG. 17 further illustrates the embodiment of the screen for building the pulse.

At 1404, one or more pulses are defined. FIGS. 16 and 17 illustrate an embodiment of the screen for building a pulse. The screen displays pulse tags P1-P3 indicating that 3 pulses are stored and a new pulse tag "+" allowing the user to define a new pulse and add it to the stored pulses. In the example as illustrated in FIGS. 16 and 17, in response to the pulse tag P1 being selected, the GUI displays the field (F2) assigned to the pulse P1 and the pulse width (PW) of the pulse P1, as shown in FIG. 16. The user may select the field and/or the pulse width to make modification(s) and/or select an advanced pulse editing ("Adv Pulse") option. In response to the advanced pulse editing option being selected, the GUI displays a graphical representation of the pulse P1, as shown in FIG. 17. The user is then allowed to modify the pulse P1 by editing the graphical representation, such as by dragging a horizontal segment of the displayed waveform to change the amplitude associated with that segment and/or a vertical segment of the of the displayed waveform to change the timing associated with that segment. Under the advanced pulse editing option, the GUI provides a command menu providing the user with pulse editing options. Examples of the commands, as illustrated in FIG. 17, include "Open" (which allows the user to open another stored waveform for use as a template, for example) and "Save" (which allows the user to save a newly defined or modified pulse).

Figure 18:
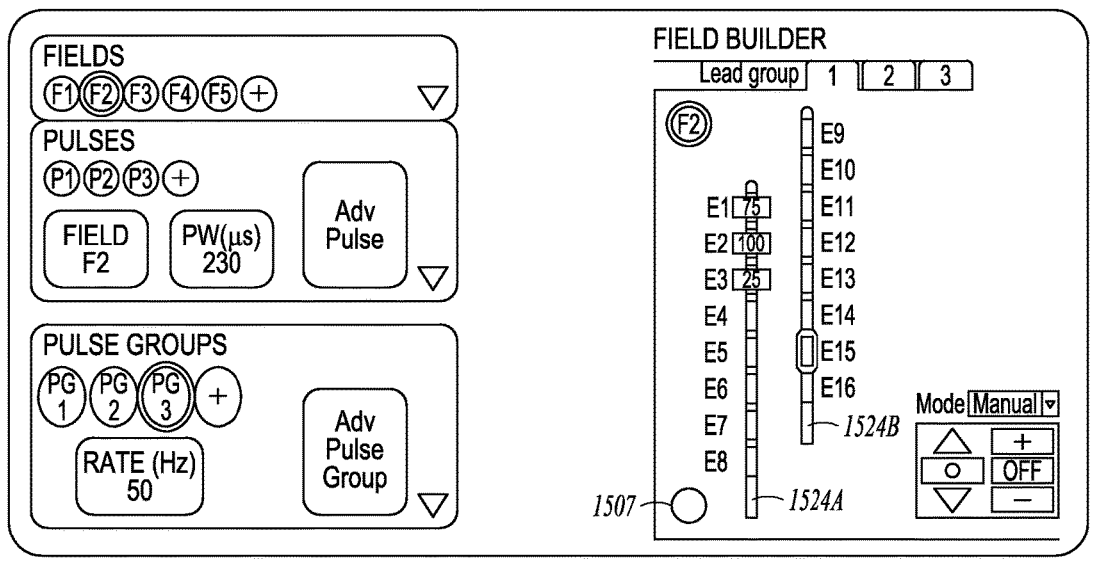
FIG. 18 illustrates an embodiment of the screen for building a PG.
Figure 19:
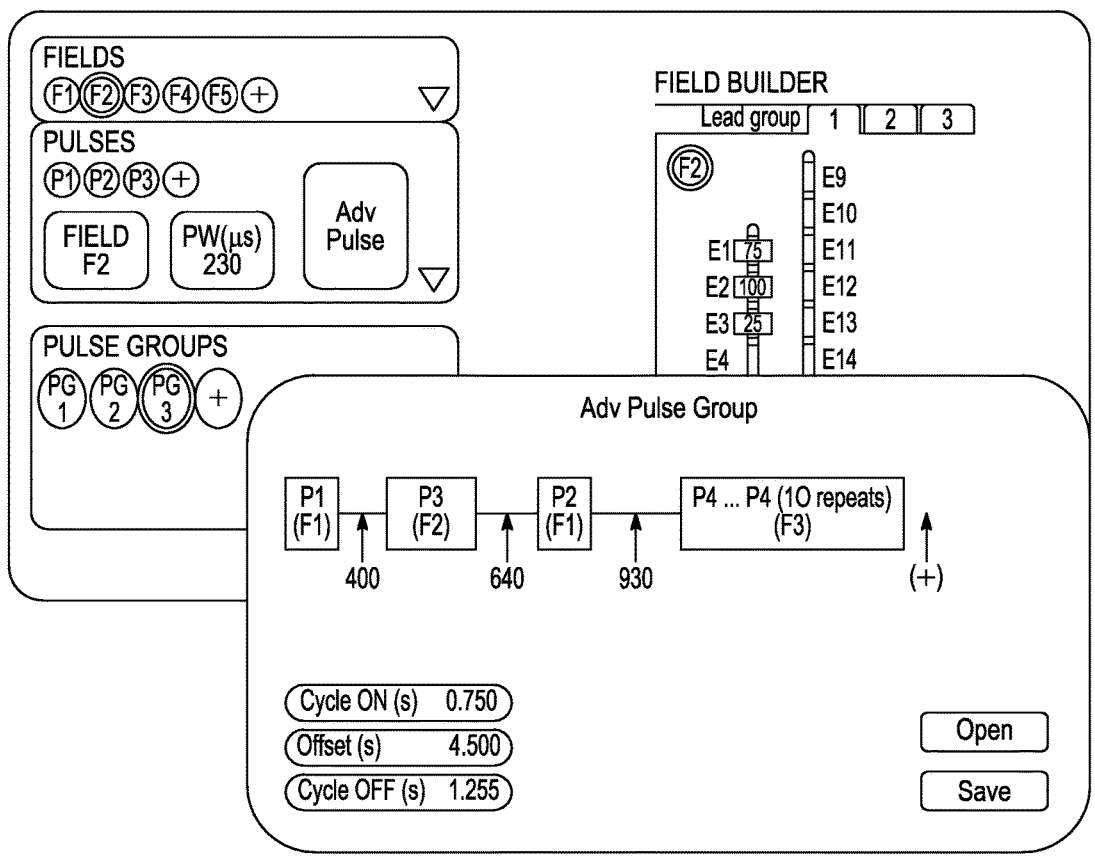
FIG. 19 further illustrates the embodiment of the screen for building the PG.

At 1406, one or more PGs are defined. FIGS. 18 and 19 illustrate an embodiment of the screen for building a PG. The screen displays PG tags PG1-PG3 indicating that 3 PGs are stored and a new PG tag "+" allowing the user to define a new PG and add it to the stored PGs. In the example as illustrated in FIGS. 18 and 19, in response to the tag PG3 being selected, the GUI displays the rate (delivery frequency) assigned to the PG1, as shown in FIG. 18. The user may select the rate to change the frequency of PG delivery and/or select an advanced PG editing ("Adv Pulse Group") option. In response to the advanced PG editing option being selected, the GUI displays a graphical representation of the PG3, as shown in FIG. 19. The user is then allowed to modify the pulse group PG3 by editing its graphical representation. In the illustrated embodiment, the PG is defined by specifying pulses, which may be repeated, and inter-pulse intervals between adjacent pulses. For example, as illustrated in FIG. 19, the PG being adjusted includes a first pulse P1 (to which field F1 is assigned) that starts after an offset of 4.5 seconds, a second pulse P3 (to which field F2 is assigned) that starts after an inter-pulse interval of 400 milliseconds (which starts at the end of the first pulse P1, a third pulse P2 (to which field F1 is assigned) that starts after an inter-pulse interval of 640 milliseconds (which starts at the end of the first pulse P1, and then 10 pulses being the pulse P4 (to which field F3 is assigned) is repeated 10 times after an inter-pulse interval of 930 milliseconds (which starts at the end of the third pulse P2. At the end of the 10 repeated pulses P4, a "(+)" sign allows the user to add more pulses and inter-pulse intervals to the pulse group PG3. "Cycle ON(s)" and "Cycle OFF (s)" allow the user to specify periods during which delivery of the pulses from the PG is turned on (and repeating when necessary) and off, respectively. Under the advanced PG editing option, the GUI provides a command menu providing the user with PG editing options. Examples of the commands, as illustrated in FIG. 17, include "Open" (which allows the user to open another stored waveform for use as a template, for example) and "Save" (which allows the user to save a newly defined or modified pulse).

Figure 20:
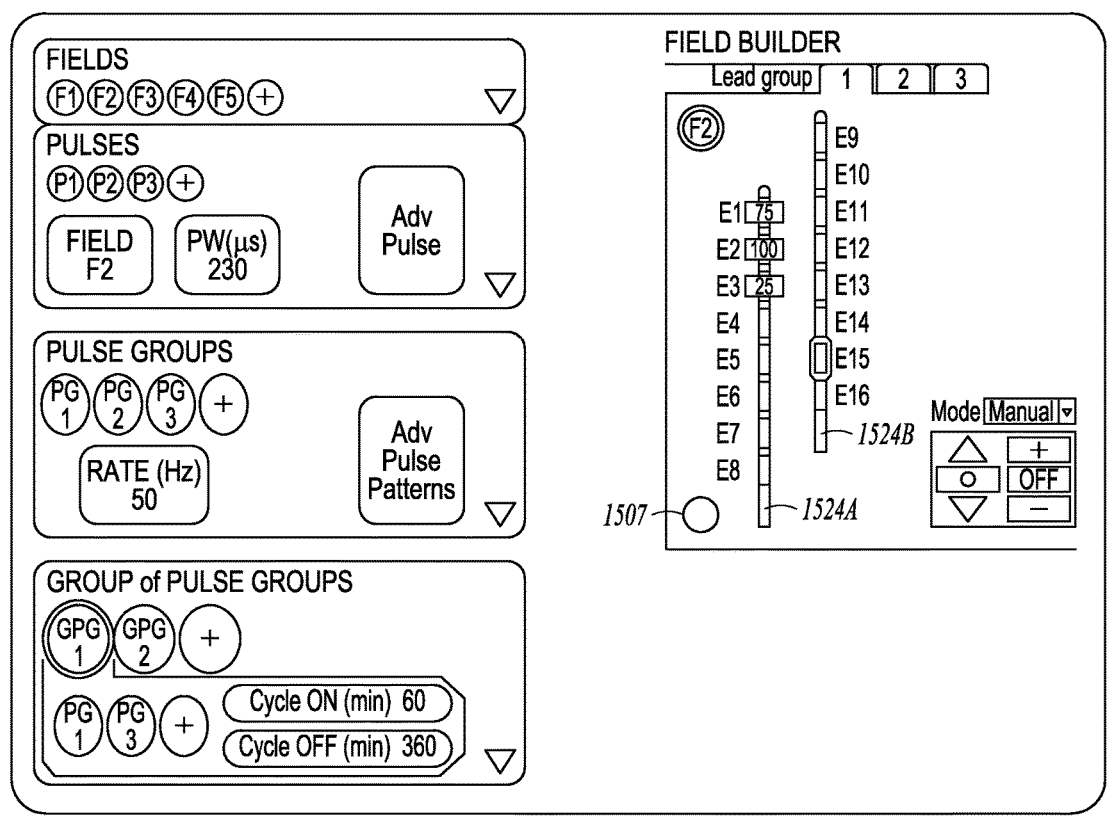
FIG. 20 illustrates embodiment of the screen for building a GPG.

At 1408, one or more GPGs are defined. FIG. 20 illustrates embodiment of the screen for building a GPG. The screen displays GPG tags GPG1 and GPG2 indicating that 2 PGs are stored and a new GPG tag "+" allowing the user to define a new GPG and add it to the stored GPGs. In the example as illustrated in FIG. 20, in response to the tag GPG1 being selected, the GUI displays the PGs included in GPG1 (showing PG1 and PG3 being included as an example) and the duty cycle at which GPG1 is to be delivered. The user may modify the selection of the PGs as well as the ON and OFF durations of the duty cycle.

At 1410, a pattern of neurostimulation pulses is defined. In one embodiment, the pattern includes the GPG1 that includes PG1 and PG3 and is repeatedly delivered at an ON-period of 60 minutes followed by an OFF-period of 360 minutes. In other words, the neurostimulation includes delivery of GPG1 repeated for an hour on a 7-hour periodic basis. In various embodiments, the pattern of neurostimulation pulses can be defined in any combination of stored GPGs, inter-GPG timing parameters, and therapy session timing parameters. In various other embodiments, the pattern of neurostimulation pulses can be defined in any combination of stored pulses, PGs, GPGs, and various timing parameters controlling relative timing of the selected pulses, PGs, and/or GPGs as well as timing of therapy session.

Figure 21:
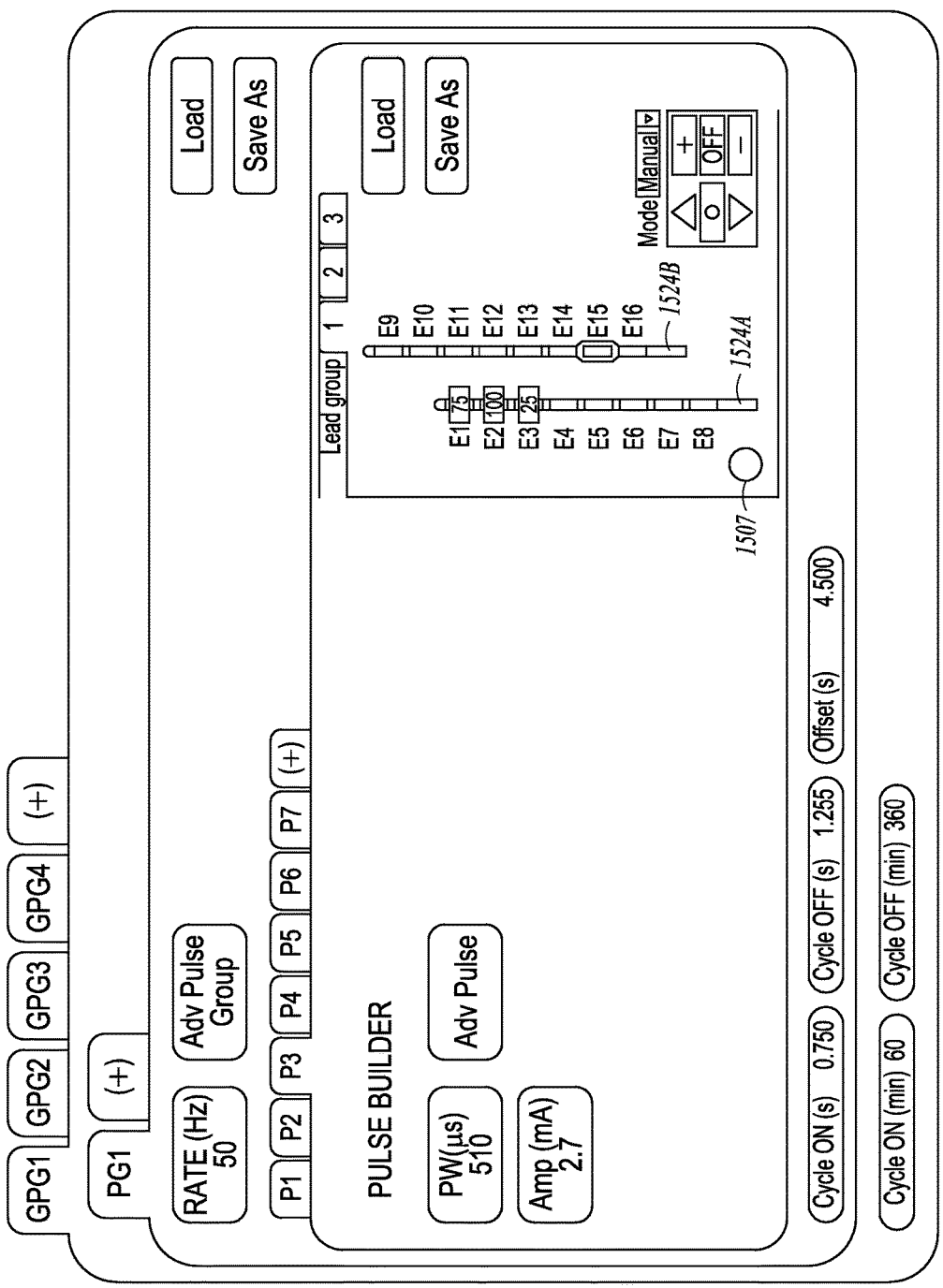
FIG. 21 illustrates an embodiment of a screen of a GUI allowing for access to pulses, PGs, and GPGs.
Figure 22:
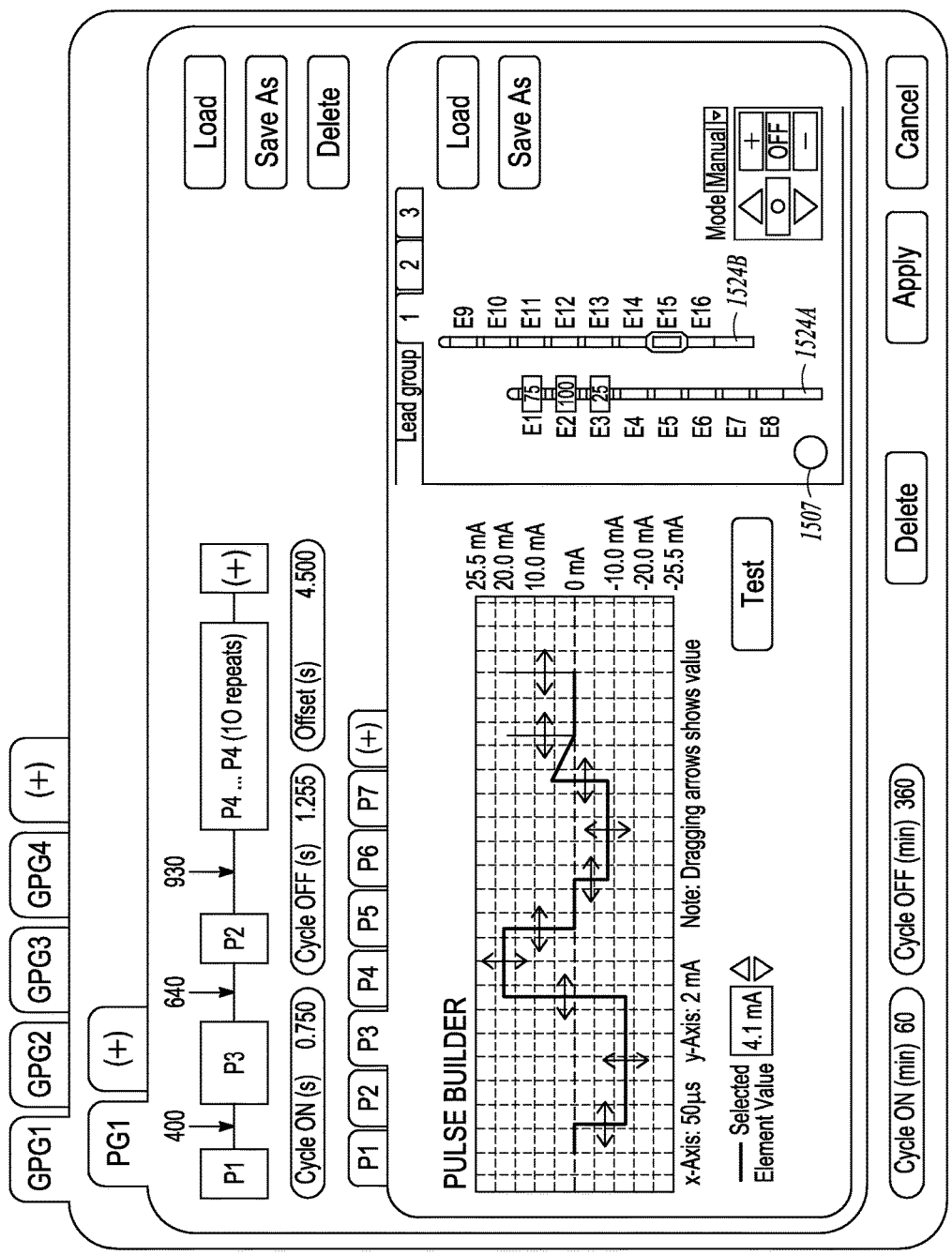
FIG. 22 illustrates an embodiment of a screen of a GUI allowing for access to pulses, PGs, and GPGs.
Figure 23:
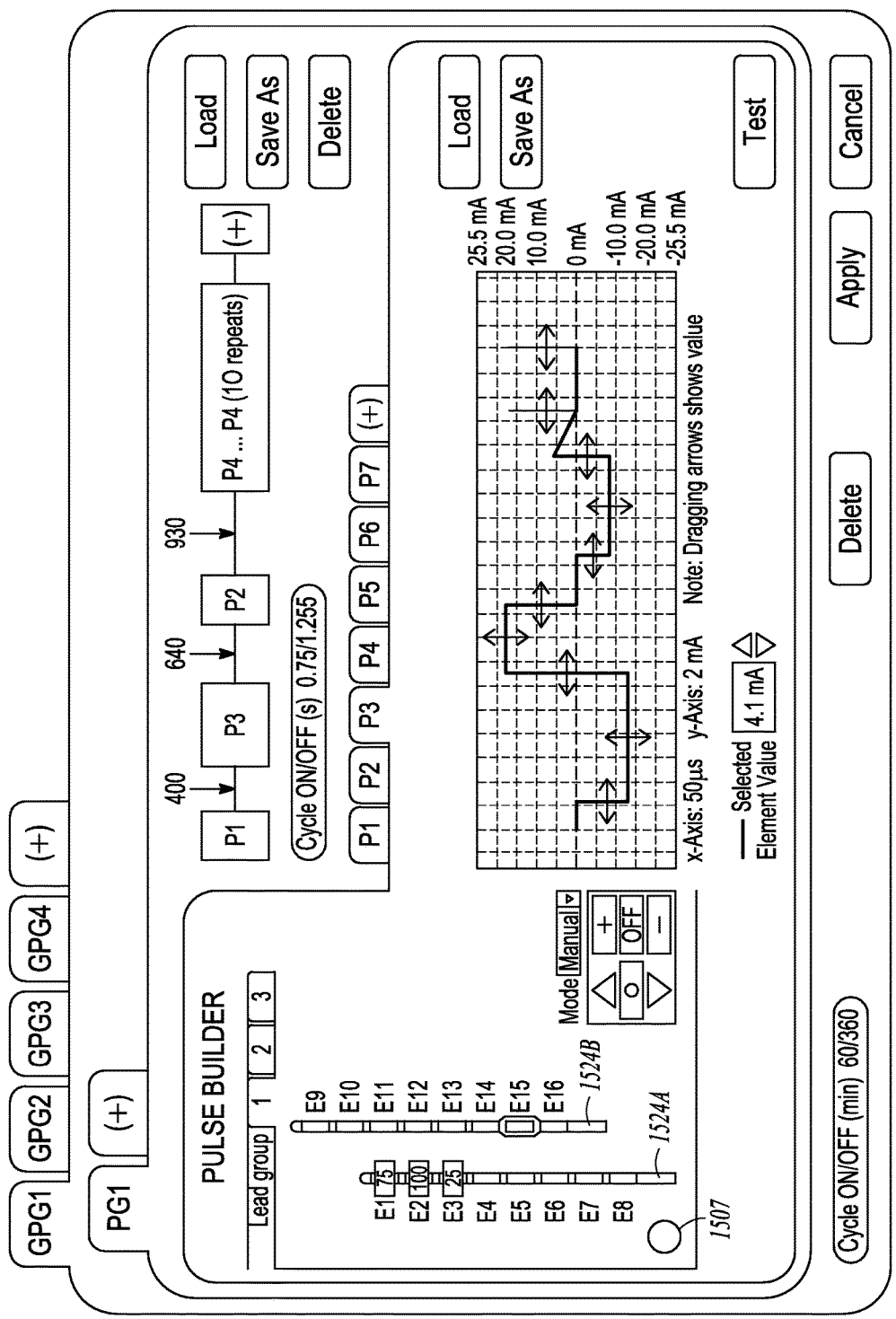
FIG. 23 illustrates an embodiment of a screen of a GUI allowing for access to pulses, PGs, and GPGs.

FIGS. 21-23 illustrate various embodiments of a screen of the GUI that allows for access to pulses, PGs, and GPGs. The screen combines the programming functions of the screens illustrated in FIGS. 15-20 but allows the user to access to any of the stored pulses, PGs, and GPGs, as well as allowing the user to add new pulses, PGs, and GPGs, on one single screen.

FIG. 21 illustrates an embodiment of the screen allowing for access to pulses, PGs, and GPGs. In the illustrated embodiment, the waveform tags (including pulse tags P1-P7 and new pulse tag "(+)", PG tag PG1 and new PG tag "(+)", and GPG tags GPG1-GPG4 and new GPG tag "(+)") are each displayed as a tab for a folder that opens into a corresponding waveform builder. The "Load" command displayed with the pulse builder allows the user to open another stored pulse for use as a pulse template, for example, and the "Save" displayed with the pulse builder allows the user to save a newly defined or modified pulse. The "Load" command displayed with the PG builder allows the user to open another stored PG for use as a pulse template, for example, and the "Save" displayed with the PG builder allows the user to save a newly defined or modified PG.

FIGS. 22 and 23 each illustrate another embodiment of the screen allowing for access to pulses, PGs, and GPGs. The screens of FIGS. 22 and 23 each include all the functions and visual features illustrated in FIGS. 15-21, with the difference being designs of the layout of the features. In various embodiments, the layout of the features may be designed for selection based on the user's visual preference. Several additional command buttons are illustrated in FIGS. 22 and 23 as further examples of user commands that may be provided in the GUI. The "Save As" command allows the user to modify a pulse or PG and save (add to the stored waveforms) as a new pulse or PG, respectively. The "Apply" button applies a selected GPG with duty cycle parameters as the pattern of neurostimulation pulses for programming the stimulation device. The "Test" button allows the stimulation device to deliver only the accessed waveform (such as a selected pulse or PG) in a "tonic" mode for testing purposes.

In the illustrated embodiment, the pulse builder allows the user to modify the pulse waveform by visually editing its graphical representation. The arrows on the pulse waveform indicate how each segment can be modified by dragging. In one embodiment, the entire pulse waveform may be selected for scaling.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for controlling delivery of neurostimulation by a user, comprising:
 a storage device configured to store individually definable waveforms;
 a programming control circuit configured to generate stimulation parameters for programming a neurostimulation device to deliver the neurostimulation pulses according to a pattern of neurostimulation pulses; and
 a graphical user interface (GUI) coupled to the storage device and the programming control circuit and configured to allow the user to graphically create a new waveform to be added to the stored individually definable waveforms and to allow the user to define the pattern of the neurostimulation pulses by selecting one or more first waveforms from the stored individually definable waveforms to be included in the pattern of the neurostimulation pulses and selecting one or more second waveforms from the one or more first waveforms to be each repeated for a specified number of times in the pattern of the neurostimulation pulses.

2. The system of claim 1, wherein the stored individually definable waveforms comprise stored pulses, and the GUI is configured to allow the user to define each pulse in the pattern of the neurostimulation pulses by selecting a pulse from the stored pulses or repeating a defined pulse.

3. The system of claim 2, wherein the GUI is configured to allow the user to edit each pulse of the stored pulses.

4. The system of claim 2, wherein the GUI is configured to allow the user to define timing of each pulse in the pattern of the neurostimulation pulses.

5. The system if claim 2, wherein the stored individually definable waveforms further comprise one or more pulse groups (PGs) each including one or more pulses selected from the stored pulses, and the GUI is configured to allow the user to define each PG by selecting one or more first pulses from the stored pulses to be included in the each PG and selecting one or more second pulses from the one or more first pulses to be each repeated for a specified number of times in the each PG.

6. The system of claim 5, wherein the stored individually definable waveforms further comprise one or more groups of pulse groups (GPGs) each including one or more PGs selected from the stored one or more PGs, and the GUI is configured to allow the user to define each GPG by selecting one or more PGs to be included in the each GPG.

7. The system of claim 6, wherein the GUI is configured to allow the user to edit each waveform of the stored individually definable waveforms.

8. The system of claim 7, wherein the GUI is configured to allow for export of a waveform selected from the stored individually definable waveforms from the system and import of a waveform into the system to be added to the stored individually definable waveforms.

9. A method for controlling neurostimulation, comprising:
storing individually definable waveforms in a storage device;
providing a graphical user interface (GUI) allowing new waveforms to be graphically created and added to the stored individually definable waveforms;
receiving from a user using the GUI a selection of one or more first waveforms from the stored individually definable waveforms to be included in a pattern of neurostimulation pulses;
receiving from the user using the GUI a selection of one or more second waveforms from the one or more first waveforms to be each repeated for a specified number of times in the pattern of the neurostimulation pulses; and
generating stimulation parameters for programming a neurostimulation device to deliver the neurostimulation according to the pattern of the neurostimulation pulses.

10. The method of claim 9, further comprising programming an implantable neurostimulation device using the generated stimulation parameters.

11. The method of claim 9, wherein the stored individually definable waveforms comprise one or more stored pulses.

12. The method of claim 11, comprising:
organizing the stored individually definable waveforms into a hierarchical structure including a plurality of levels; and
allowing the user to define each waveform of each level of the plurality of levels using one or more waveforms of one or more lower levels.

13. The method of claim 12, wherein the stored individually definable waveforms further comprise one or more pulse groups (PGs) each including one or more pulses selected from the stored pulses.

14. The method of claim 13, wherein the stored individually definable waveforms further comprise one or more groups of pulse groups (GPGs) each including one or more PGs selected from the stored one or more PGs.

15. The method of claim 14, further comprising exporting a waveform selected from the stored individually definable waveforms for sharing with one or more other users.

16. The method of claim 14, further comprising importing a waveform from another user to be added to the stored individually definable waveforms.

17. The method of claim 9, further comprising:
receiving from the user a selection of a waveform from the stored individually definable waveforms; and
allowing the user to graphically edit the selected waveform using the GUI.

18. A non-transitory computer-readable storage medium including instructions, which when executed by a system, cause the system to perform a method for controlling neurostimulation, the method comprising:
storing individually definable waveforms in a storage device;
providing a graphical user interface (GUI) allowing new waveforms to be graphically created and added to the stored individually definable waveforms;
receiving from a user using the GUI a selection of one or more first waveforms from the stored individually definable waveforms to be included in a pattern of neurostimulation pulses;
receiving from the user using the GUI a selection of one or more second waveforms from the one or more first waveforms to be each repeated for a specified number of times in the pattern of the neurostimulation pulses; and
generating stimulation parameters for programming a neurostimulation device to deliver the neurostimulation according to the pattern of the neurostimulation pulses.

19. The non-transitory computer-readable storage medium of claim 18, wherein the method further comprises:
organizing the stored individually definable waveforms into a hierarchical structure including a plurality of levels; and
allowing the user to define each waveform of each level of the plurality of levels using one or more waveforms of one or more lower levels.

20. The non-transitory computer-readable storage medium of claim 18, wherein the method further comprises at least one of:
exporting a waveform selected from the stored individually definable waveforms for sharing with one or more other users; or
importing a waveform from another user to be added to the stored individually definable waveforms.

* * * * *